United States Patent
Sugiyama et al.

(10) Patent No.: US 9,706,943 B2
(45) Date of Patent: Jul. 18, 2017

(54) IMAGE DISPLAY APPARATUS, IMAGE DISPLAY METHOD, AND MAGNETIC RESONANCE IMAGING APPARATUS

(75) Inventors: Atsuko Sugiyama, Nasushiobara (JP); Hitoshi Yamagata, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 136 days.

(21) Appl. No.: 12/603,961

(22) Filed: Oct. 22, 2009

(65) Prior Publication Data

US 2010/0106002 A1 Apr. 29, 2010

(30) Foreign Application Priority Data

Oct. 24, 2008 (JP) ................................ 2008-274842
Sep. 9, 2009 (JP) ................................ 2009-208519

(51) Int. Cl.
*A61B 5/00* (2006.01)
*A61B 5/055* (2006.01)
(Continued)

(52) U.S. Cl.
CPC .............. *A61B 5/055* (2013.01); *A61B 6/032* (2013.01); *A61B 6/463* (2013.01); *A61B 6/469* (2013.01); *G01R 33/56* (2013.01); *G01R 33/56366* (2013.01); *A61B 5/7425* (2013.01); *A61B 6/481* (2013.01); *A61B 6/507* (2013.01);
(Continued)

(58) Field of Classification Search
USPC ....... 600/407, 410, 411, 414, 415, 420, 421; 324/309, 318
See application file for complete search history.

(56) References Cited

U.S. PATENT DOCUMENTS

2002/0072672 A1 6/2002 Roundhill et al.
2006/0058624 A1* 3/2006 Kimura .................... 600/407
(Continued)

FOREIGN PATENT DOCUMENTS

CN 1242977 A 2/2000
CN 1775171 A 5/2006
(Continued)

OTHER PUBLICATIONS

Office Action dated Jun. 27, 2011 in Chinese Application No. CN 200910207021.
(Continued)

*Primary Examiner* — Amanda Lauritzen Moher
(74) *Attorney, Agent, or Firm* — Nixon & Vanderhye P.C.

(57) ABSTRACT

According to an Magnetic Resonance Imaging (MRI) apparatus, a Region Of Interest (ROI) setting unit included in a control unit sets an ROI on each of a $T_1$ weighted image, a $T_2$ weighted image, and a flair image of a brain of a subject; and a feature-analysis processing unit creates a histogram of statistics with respect to each of a plurality of images based on pixel values of pixels included in the ROI set by the ROI setting unit. A display control unit then causes a display unit to display the images in the substantially same position in a display area included in the display unit by switching the images in a certain order, and to display the histogram created by the feature-analysis processing unit in the same display area.

11 Claims, 14 Drawing Sheets

(51) Int. Cl.
  *A61B 6/03* (2006.01)
  *A61B 6/00* (2006.01)
  *G01R 33/56* (2006.01)
  *G01R 33/48* (2006.01)
  *G01R 33/563* (2006.01)

(52) U.S. Cl.
  CPC ...... *G01R 33/4806* (2013.01); *G01R 33/5602* (2013.01); *G01R 33/5608* (2013.01); *G01R 33/56341* (2013.01)

(56) References Cited

U.S. PATENT DOCUMENTS

| | | | |
|---|---|---|---|
| 2007/0176601 A1* | 8/2007 | Adachi | 324/310 |
| 2008/0009707 A1* | 1/2008 | Theriault | 600/410 |
| 2008/0086028 A1 | 4/2008 | Matsui | |
| 2009/0034812 A1* | 2/2009 | Nowinski et al. | 382/131 |
| 2009/0240136 A9 | 9/2009 | Sun et al. | |
| 2009/0299172 A1* | 12/2009 | Corot et al. | 600/420 |

FOREIGN PATENT DOCUMENTS

| | | |
|---|---|---|
| CN | 101023871 A | 8/2007 |
| JP | 63-317144 | 12/1988 |
| JP | 1-291826 | 11/1989 |
| JP | 08-076741 | 3/1996 |
| JP | 2006-095279 | 4/2006 |
| JP | 2007-029248 | 2/2007 |
| JP | 2008-136871 | 6/2008 |
| WO | 2007/052634 A1 | 5/2007 |

OTHER PUBLICATIONS

Office Action mailed Sep. 10, 2013 in JP Application No. 2009-208519 with English translation.
Office Action dated Nov. 15, 2014, in CN 201210007869.X.
Office Action dated Jan. 10, 2014 in U.S. Appl. No. 13/493,242, Sugiyama et al.
Office Action mailed Dec. 18, 2015 in U.S. Appl. No. 13/493,242.

* cited by examiner

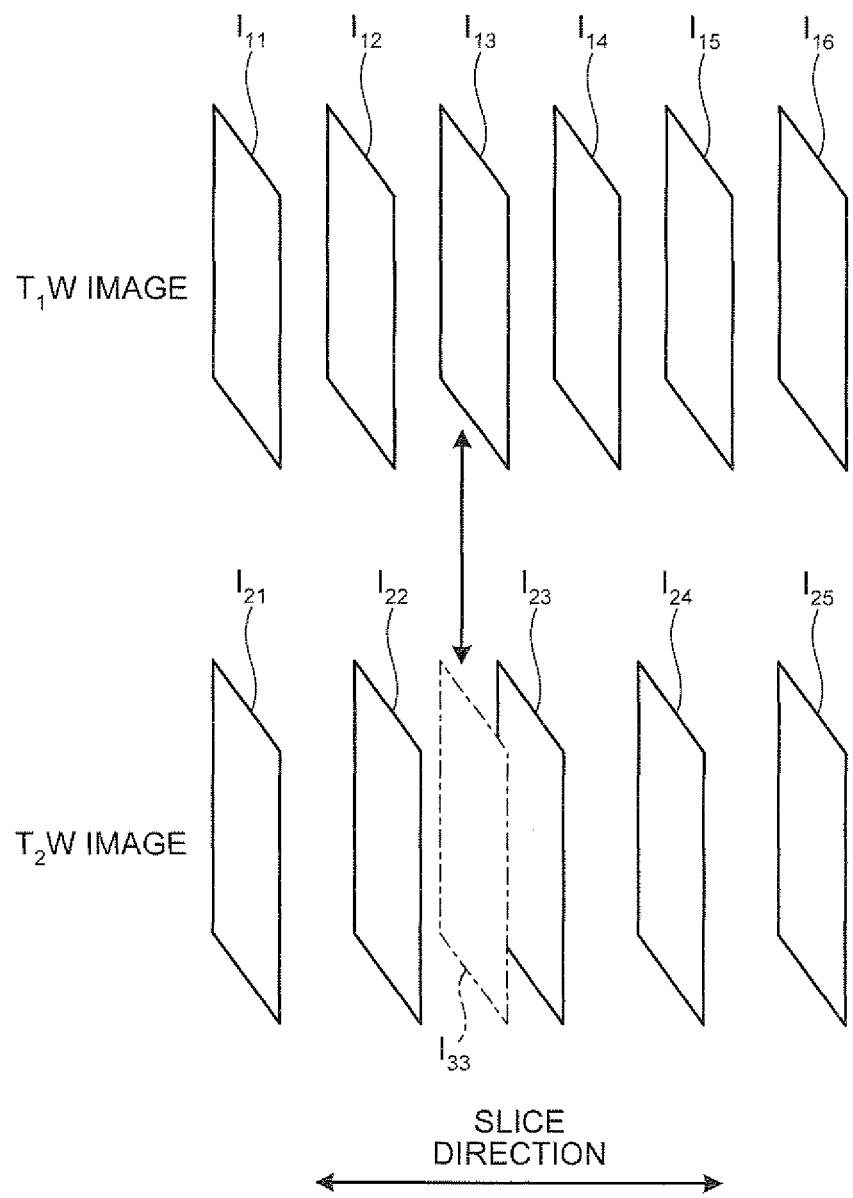

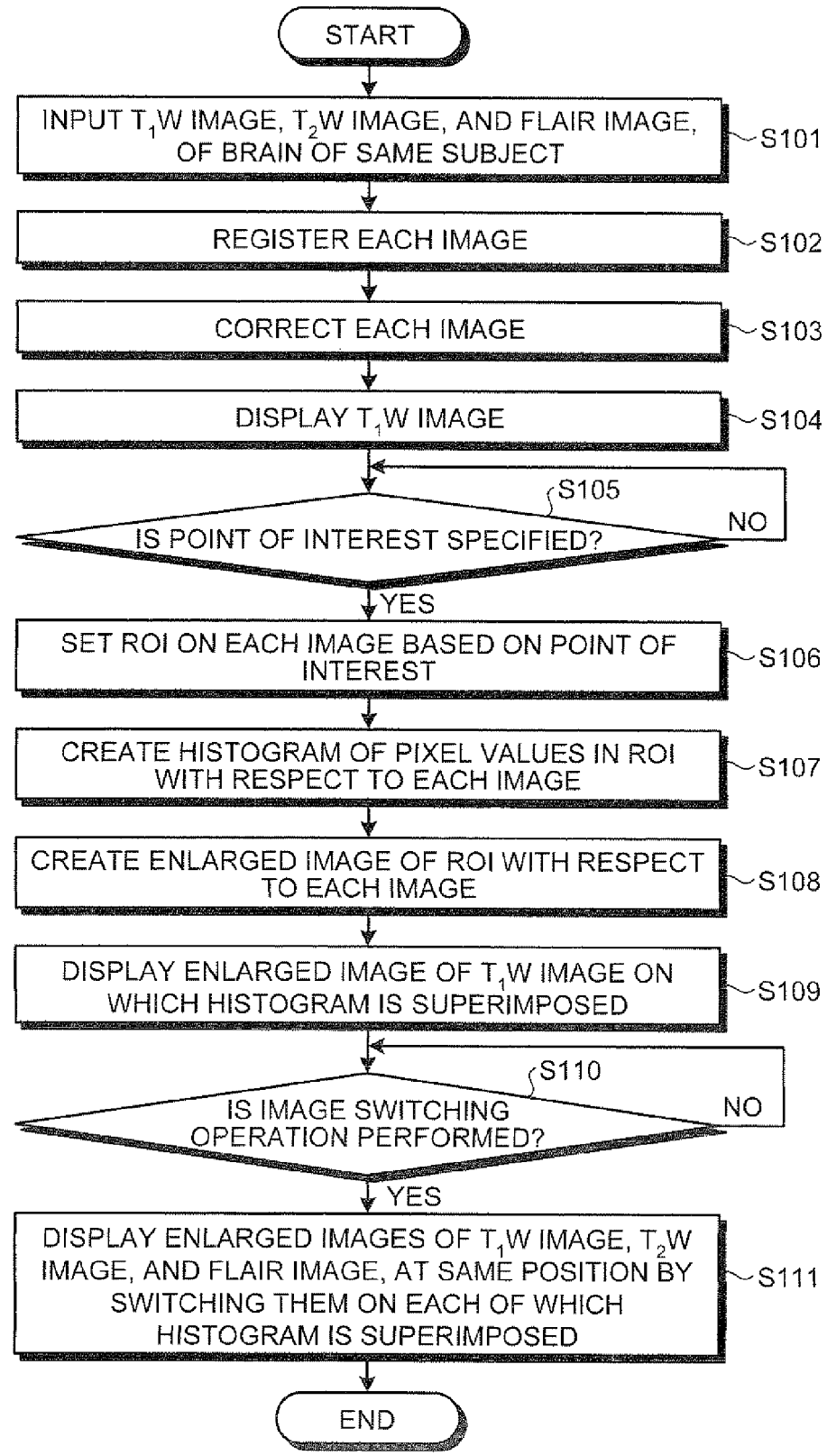

IMAGE DISPLAY APPARATUS, IMAGE DISPLAY METHOD, AND MAGNETIC RESONANCE IMAGING APPARATUS

CROSS-REFERENCE TO RELATED APPLICATIONS

This application is based upon and claims the benefit of priority from the prior Japanese Patent Application No. 2008-274842, filed on Oct. 24, 2008, and No. 2009-208519, filed on Sep. 9, 2009; the entire contents of which are incorporated herein by reference.

BACKGROUND

1. Technical Field

The present exemplary embodiments relate to an image display apparatus, an image display method, and a magnetic resonance imaging apparatus, and particularly relate to an image display apparatus, an image display method, and a magnetic resonance imaging apparatus according to which change in details due to a difference of the imaging methods can be easily observed without moving the observation point between images.

2. Description of Related Art

Conventionally, various diagnoses and treatments are carried out in medical practice with the use of various images that are taken by using various diagnostic imaging apparatuses. For example, when using a Magnetic Resonance Imaging (MRI) apparatus, it can take various kinds of images, for example, a longitudinal relaxation weighted image ($T_1W$ image), a transverse relaxation weighted image ($T_2W$ image), a proton density image, a flair image, a fat suppression image, a diffusion image, a perfusion image, a functional Magnetic Resonance Imaging (f-MRI) image, and a Magnetic Resonance Spectroscopy (MRS), the list is endless. Moreover, when using an X-ray Computed Tomography (CT) apparatus, it can take a functional image, such as a functional image of a blood flow, as well as a usual anatomical image based on CT values.

Usually, when reading a plurality of different images, for example, films are arranged on a back illuminated translucent viewing surface, or images are arranged on a monitor; and then a diagnosis is carried out while the observer's eyes move from one point to another point corresponding to the same anatomical portion between respective images. According to such diagnosis, because images are read by moving the observer's eyes to respective regions of interest among several kinds of arranged images, it takes a long time to read the images. It is also very difficult to perform a diagnosis while comparing anatomical details between images because it is carried out with movement of the observation point.

For this reason, for example, an ultrasound diagnosis apparatus uses a method of superimposing and displaying a monochrome image and a color image onto both of which the same portion is imaged, which is called a fusion method. Apart from this, another method is proposed of enabling a comparative reading without movement of the observation point when there is a plurality of images taken of the same portion, by displaying the images in substantially the same position on a screen by switching the images one by one (for example, see JP-A 2006-95279 (KOKAI)).

However, according to the conventional technology, it is difficult to observe easily change in details due to a difference of imaging methods. For example, according to display by a fusion method, because at least two images are superimposed, one of the superimposed images is limited to an image of a small spatial resolution, such as a monochrome image, or a topical image. According to the method of displaying images in the substantially same position by switching them, although reduction in movement of observation point is taken into account, observation of change in details due to a difference of imaging methods is not considered.

SUMMARY OF EXEMPLARY EMBODIMENTS

According to one aspect of the present invention, an image display apparatus includes a region-of-interest setting unit that sets a region of interest on each of a plurality of images that is imaged by a diagnostic imaging apparatus and includes a same portion of a subject; a feature analysis unit that performs a feature analysis on each of the images based on pixel values of pixels included in the region of interest set by the region-of-interest setting unit; and a display control unit that causes a display unit to display the images in a substantially same position in a display area included in the display unit by switching the images in an order prescribed, and to display a result of the feature analysis obtained by the feature analysis unit in same display area.

According to another aspect of the present invention, an image display apparatus includes a mode changing unit that changes a display mode of image with respect to each of a plurality of images that is imaged by a diagnostic imaging apparatus and includes a same portion of a subject; and a display control unit that causes a display unit to display the images of each of which the display mode is changed by the mode changing unit in a substantially same position in a display area included in the display unit by switching the images in an order prescribed.

According to still another aspect of the present invention, an image display method includes setting a region of interest on each of a plurality of images that is imaged by a diagnostic imaging apparatus and includes a same portion of a subject; performing a feature analysis on each of the images based on pixel values of pixels included in the region of interest; and causing a display unit to display the images in a substantially same position in a display area included in the display unit by switching the images in an order prescribed, and to display a result of the feature analysis in same display area.

According to still another aspect of the present invention, an image display method includes changing a display mode of image with respect to each of a plurality of images that is imaged by a diagnostic imaging apparatus and includes a same portion of a subject; and causing a display unit to display the images of each of which the display mode is changed, by switching the images in an order prescribed, in a substantially same position in a display area included in the display unit.

According to still another aspect of the present invention, a magnetic resonance imaging apparatus includes an imaging unit that takes a plurality of images that includes a same portion of a subject; a region-of-interest setting unit that sets a region of interest on each of the images taken by the imaging unit; a feature analysis unit that performs a feature analysis on each of the images based on pixel values of pixels included in the region of interest set by the region-of-interest setting unit; and a display control unit that causes a display unit to display the images in a substantially same position in a display area included in the display unit by switching the images in an order prescribed, and to display a result of the feature analysis obtained by the feature analysis unit in same display area.

According to still another aspect of the present invention, a magnetic resonance imaging apparatus includes an imaging unit that takes a plurality of images that includes a same portion of a subject; a mode changing unit that changes a display mode of image with respect to each of the images taken by the imaging unit; and a display control unit that causes a display unit to display the images of which the display mode is changed by the mode changing unit, by switching the images in an order prescribed, in a substantially same position in a display area included in the display unit.

BRIEF DESCRIPTION OF THE DRAWINGS

FIG. 4 is a schematic diagram for explaining of another example of an image registration method performed by the registration processing unit according to the first embodiment;

FIG. 5 is a flowchart of a process procedure of image display performed by a control unit according to the first embodiment;

DETAILED DESCRIPTION OF EXEMPLARY EMBODIMENTS

Exemplary embodiments of an image display apparatus, an image display method, and a magnetic resonance imaging apparatus according to the present invention will be explained below in detail with reference to the accompanying drawings. Hereinafter, a Magnetic Resonance Imaging apparatus is referred to as an MRI apparatus.

Figure 1:
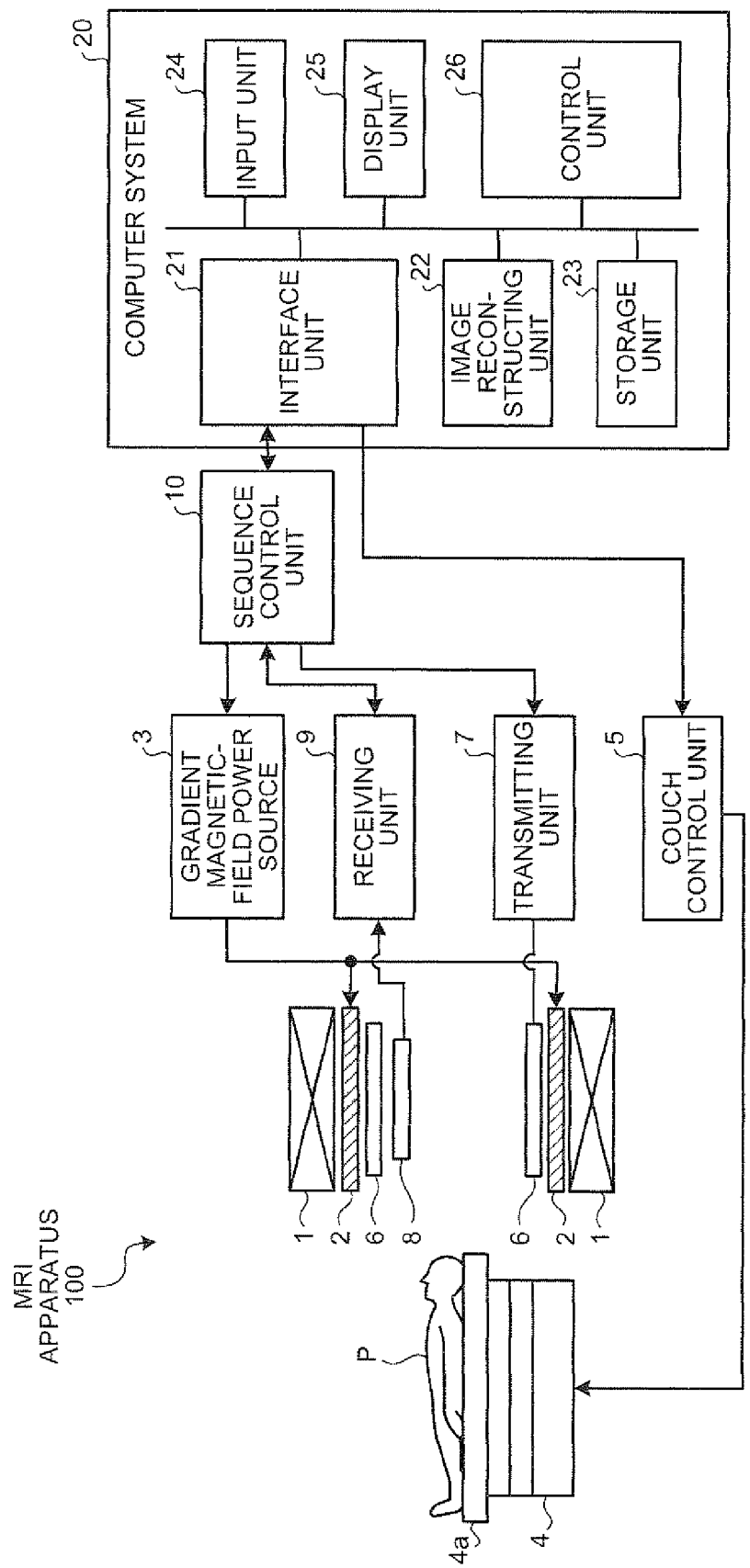
FIG. 1 is a schematic diagram of a general configuration of a Magnetic Resonance Imaging (MRI) apparatus according to a first embodiment of the present invention.

A first embodiment according to the present invention is explained below about an MRI apparatus to which the present invention is applied. First of all, a general configuration of an MRI apparatus 100 according to the first embodiment is explained below with reference to FIG. 1. FIG. 1 is a schematic diagram of a general configuration of the MRI apparatus 100 according to the first embodiment. As shown in FIG. 1, the MRI apparatus 100 includes a static magnetic-field magnet 1, a gradient magnetic-field coil 2, a gradient magnetic-field power source 3, a couch 4, a couch control unit 5, a Radio Frequency (RF) transmitting coil 6, a transmitting unit 7, an RF receiving coil 8, a receiving unit 9, a sequence control unit 10, and a computer system 20.

The static magnetic-field magnet 1 is a magnet formed in a hollow drum shape, and generates a uniform static magnetic field in its inside space. For example, a permanent magnet, or a super conducting magnet is used as the static magnetic-field magnet 1.

The gradient magnetic-field coil 2 is a coil formed in a hollow drum shape, and is arranged on the inner side of the static magnetic-field magnet 1. The gradient magnetic-field coil 2 is formed of three coils in combination corresponding to x, y, and z axes orthogonal to one another; and the three coils generate gradient magnetic fields of which field strengths vary along three directions of the x, y, and z axes, respectively, by individually receiving a current supply from the gradient magnetic-field power source 3, which will be described later. It is assumed that the z axis direction is the same direction as that of the static magnetic field. The gradient magnetic-field power source 3 is a device that supplies a current to the gradient magnetic-field coil 2.

The gradient magnetic fields of the x, y, and z axes generated by the gradient magnetic-field coil 2 correspond to, for example, a slice-selective gradient magnetic field Gs, a phase-encoding gradient magnetic field Ge, and a readout gradient magnetic field Gr, respectively. The slice-selective gradient magnetic field Gs is used for arbitrarily setting a scan cross section. The phase-encoding gradient magnetic field Ge is used for changing the phase of a magnetic resonance signal in accordance with a spatial position. The readout gradient magnetic field Gr is used for changing the frequency of a magnetic resonance signal in accordance with a spatial position.

The couch 4 is a device that includes a top plate 4a on which a subject P is to be placed; and under the control of the couch control unit 5, which will be described later, the couch 4 inserts the top plate 4a on which the subject P is placed, into a hole (a scanning space) of the gradient magnetic-field coil 2. Usually, the couch 4 is placed such that the longitudinal direction of the couch 4 is to be parallel to the central axis of the static magnetic-field magnet 1. The couch control unit 5 is a device that controls the couch 4 under the control of a control unit 26, and moves the top plate 4a in the longitudinal direction and upward and downward by driving the couch 4.

The RF transmitting coil 6 is a coil arranged on the inner side of the gradient magnetic-field coil 2, and generates a radio-frequency magnetic field by receiving supply of a radio-frequency pulse from the transmitting unit 7. The transmitting unit 7 is a device that transmits a radio-frequency pulse corresponding to a Larmor frequency to the RF transmitting coil 6.

The RF receiving coil 8 is a coil arranged on the inner side of the gradient magnetic-field coil 2, and receives a magnetic resonance signal emitted from the subject P owing to an influence of the radio-frequency magnetic field described above. Upon receiving a magnetic resonance signal, the RF receiving coil 8 outputs the magnetic resonance signal to the receiving unit 9.

The receiving unit 9 creates k-space data based on the magnetic resonance signal output by the RF receiving coil 8. Specifically, the receiving unit 9 creates k-space data by converting a magnetic resonance signal output from the RF receiving coil 8 into digital. The k-space data is associated with information about spatial frequencies of a PE direction, an RO direction, and an SE direction by the slice-selective gradient magnetic field Gs, the phase-encoding gradient magnetic field Ge, and the readout gradient magnetic field Gr. After creating k-space data, the receiving unit 9 transmits the k-space data to the sequence control unit 10.

The sequence control unit 10 performs scanning of the subject P by activating the gradient magnetic-field power source 3, the transmitting unit 7, and the receiving unit 9, based on sequence information transmitted from the computer system 20. The sequence information defines a procedure for scanning, such as the strength of power to be supplied to the gradient magnetic-field coil 2 by the gradient magnetic-field power source 3 and the timing of supplying the power, the strength of an RF signal to be transmitted to the RF transmitting coil 6 by the transmitting unit 7 and the timing of transmitting the RF signal, and the timing of detecting a magnetic resonance signal by the receiving unit 9.

When k-space data is transmitted from the receiving unit 9 as a result of scanning the subject P by activating the gradient magnetic-field power source 3, the transmitting unit 7, and the receiving unit 9, the sequence control unit 10 transfers the k-space data to the computer system 20.

The computer system 20 performs total control of the MRI apparatus 100, data collection, image reconstruction, and the like. The computer system 20 particularly includes an interface unit 21, an image reconstructing unit 22, a storage unit 23, an input unit 24, a display unit 25, and the control unit 26.

The interface unit 21 controls input and output of various signals that are given and received to and from the sequence control unit 10. For example, the interface unit 21 transmits sequence information to the sequence control unit 10, and receives k-space data from the sequence control unit 10. When having received k-space data, the interface unit 21 stores k-space data into the storage unit 23 with respect to each subject P.

The image reconstructing unit 22 creates spectrum data of a desired nuclear spin inside the subject P or image data by performing post-processing, i.e., reconstruction processing, such as Fourier transform processing, on k-space data stored in the storage unit 23.

The storage unit 23 stores k-space data received by the interface unit 21, and image data created by the image reconstructing unit 22, with respect to each subject P.

The input unit 24 receives various instructions and information input from an operator. As the input unit 24, a pointing device, such as a mouse or a trackball, a selecting device, such as a mode switch, and an input device, such as a keyboard, can be used as required.

The display unit 25 displays various information, such as spectrum data or image data, under the control of the control unit 26. A display device, such as a liquid crystal display, can be used as the display unit 25.

The control unit 26 includes a Central Processing Unit (CPU) and a memory, both of which are not shown, and carries out total control of the MRI apparatus 100. Specifically, the control unit 26 controls a scan by creating sequence information based on imaging conditions input by the operator via the input unit 24, and transmitting the created sequence information to the sequence control unit 10, and controls reconstruction of an image performed based on k-space data sent from the sequence control unit 10 as a result of the scan.

Because Magnetic Resonance (MR) imaging is performed by using a protocol in which a plurality of different sequences are combined, different kinds of images are generally obtained through one time of imaging. Examples of a perfusion imaging protocol can be listed as follows: a $T_1$ weighted image ($T_1W$ image) imaging sequence, a $T_2$ weighted image ($T_2W$ image) imaging sequence, and a protocol in which a flair-image imaging sequence and a dynamic-image imaging sequence are combined.

The general configuration of the MRI apparatus 100 according to the first embodiment has been explained above. Under such configuration, according to the first embodiment, the control unit 26 sets a Region Of Interest (ROI) on each of a plurality of images that includes the same portion of a subject, and performs a feature analysis on each of the images based on pixel values of pixels included in the set ROI. The control unit 26 then causes the display unit 25 to display each of the images in the substantially same position in a display area included in the display unit 25 by switching the images in a certain order, and to display a result of the feature analysis in the same display area. Consequently, according to the first embodiment, change in details due to a difference of the imaging methods can be easily observed without moving observation point between images.

Figure 2:
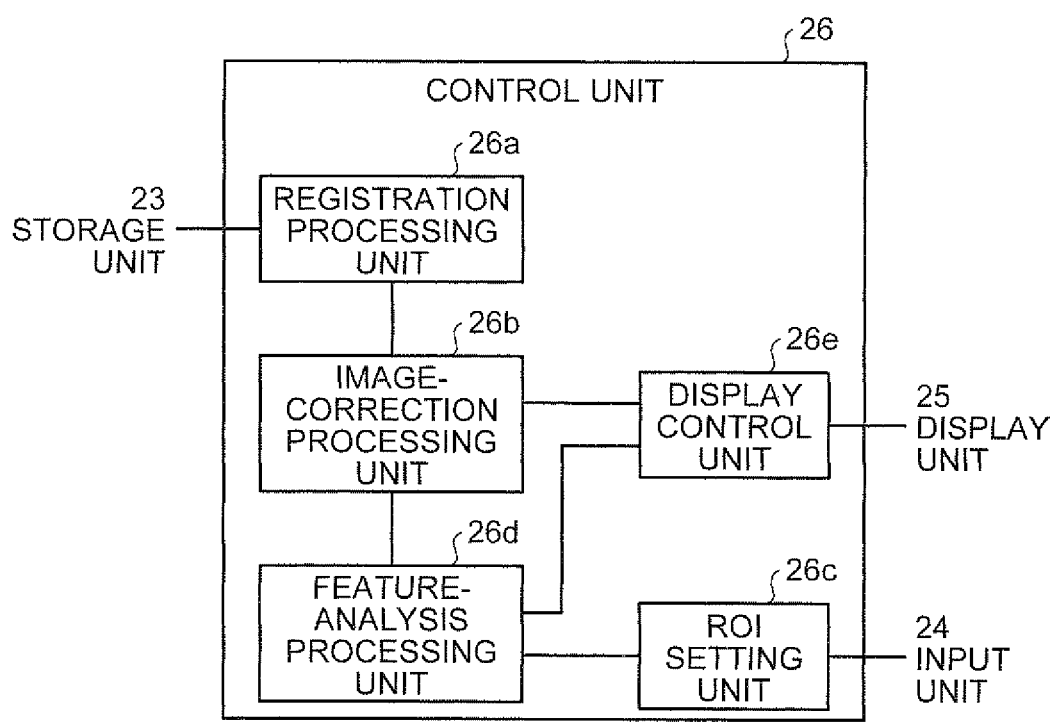
FIG. 2 is a functional block diagram of a configuration of a control unit according to the first embodiment.

Details of the control unit 26 according to the first embodiment are explained below. First of all, a configuration of the control unit 26 according to the first embodiment is explained below with reference to FIG. 2. FIG. 2 is a functional block diagram of a configuration of the control unit 26 according to the first embodiment. As shown in FIG. 2, the control unit 26 particularly includes a registration processing unit 26a, an image-correction processing unit 26b, an ROI setting unit 26c, a feature-analysis processing unit 26d, and a display control unit 26e.

The registration processing unit 26a performs registration between a plurality of images on which a portion of a subject to be examined is imaged. Specifically, the registration processing unit 26a reads from the storage unit 23 a plurality of images on which the same portion of a subject to be examined is imaged, and aligns the sizes and the positions of the read images. For the registration of images to be performed here, any of various generally-known image-registration methods, for example, registration based on anatomical information, can be used.

The registration processing unit 26a performs registration by reading a plurality of medical images, for example, different kinds of images and images along different time sequences that are taken by the same kind of diagnostic imaging apparatus through different imaging methods, or images taken by different diagnostic imaging apparatuses. For example, the registration processing unit 26a performs registration by reading images taken through different imaging methods, such as, a $T_1W$ image, a $T_2W$ image, a proton density image, a flair image, a fat suppression, image, a diffusion image, a perfusion image, a functional Magnetic Resonance Imaging (f-MRI) image, and/or an MR spectroscopy.

Moreover, for example, the registration processing unit 26a performs registration by reading images taken under imaging conditions that include a different setting value among imaging parameters. The imaging parameters include an Echo Time (TE), a Repetition Time (TR), and a b factor that indicates the strength of a Motion Probing Gradient (MPG) pulse.

Generally, an MRI apparatus can image a cross section of a subject in an arbitrary direction among three-dimensional directions. Therefore, positional information about an image taken by the MRI apparatus is expressed in a coordinate system that is uniquely determined based on a pose of a patient during a scan. Such coordinate system is called "a patient coordinate system", and is determined, with respect to each scan based on a posture of the patient (a supine position, a prone position, a right recumbent position, or a left recumbent position), and an insert direction into the apparatus (from the head, or from the foot). On the other hand, a coordinate system called "an apparatus coordinate system" is unique to an apparatus, has the origin point at the center of the magnetic field, and is expressed with three coordinate axes respectively along three directions in the apparatus, namely, an upward-and-downward direction, a right-and-left direction, and a fore-and-aft direction of the apparatus.

Morphological images, for example, a $T_1W$ image and a $T_2W$ image, are often taken of the same area in the same examination in many cases. Consequently, positions of the morphological images, such as a $T_1W$ image and a $T_2W$ image, are indicated in the same patient coordinate system. For this reason, morphological images can be easily registered by using positional information with respect to a patient coordinate system generally attached to an image.

On the other hand, functional images, for example, a diffusion image and a perfusion image, generally have a distortion, so that it is difficult to perform registration simply based on a patient coordinate system. Therefore, the registration processing unit 26a extracts a region that indicates a characteristic portion from each image, and performs registration with reference to the extracted region. FIGS. 3A to 3E are schematic diagrams for explaining an example of an image registration method performed by the registration processing unit 26a according to the first embodiment. Explained below is a case of registration between a Diffusion Weighted Imaging (DWI) image and a Perfusion Weighted Imaging (PWI) image.

Figure 3A:
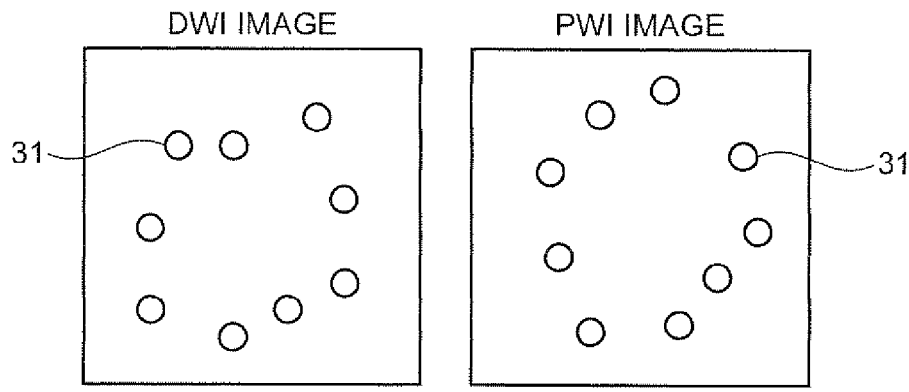
FIGS. 3A to 3E are schematic diagrams for explaining an example of an image registration method performed by a registration processing unit according to the first embodiment.

For example, to begin with, the registration processing unit 26a extracts the region of a portion subjected to registration, from each of the DWI image and a PWI image. Specifically, the registration processing unit 26a extracts the region of a portion subjected to registration from among voxels included in each of the DWI image and the PWI image by performing generally-known segmentation processing. The registration processing unit 26a then extracts voxels positioned on the boundary of the extracted region as boundary voxels 31, as shown in FIG. 3A. FIG. 3A depicts part of the boundary voxels 31.

Figure 3B:
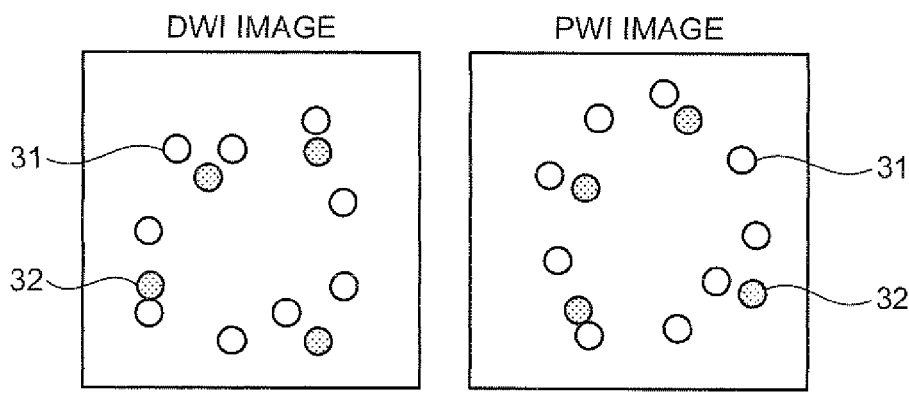
Figure 3C:
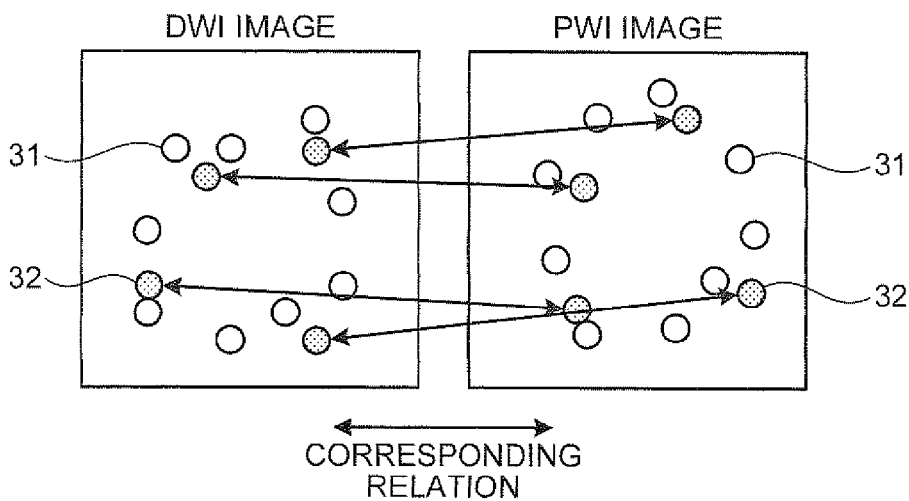

Furthermore, the registration processing unit 26a extracts shape voxels that express the shape of each region extracted from the DWI image and the PWI image. Specifically, the registration processing unit 26a selects a certain number of voxels as shape voxels 32 from among boundary voxels included in each of the DWI image and the PWI image, as shown in FIG. 3B. For example, the registration processing unit 26a selects the shape voxels 32 with certain intervals from among a plurality of boundary voxels arranged along the boundary of the region.

Subsequently, the registration processing unit 26a associates the shape voxels between the DWI image and the PWI image. Specifically, as shown in FIG. 3O, the registration processing unit 26a makes every combination of the shape voxels 32 between the DWI image and the PWI image in every pattern, and calculates a distance between combined voxels in every combination. The registration processing unit 26a then specifies a pattern of combinations of the shape voxels 32 in which the total of distances between the voxels becomes the minimum. When calculating, for example, the registration processing unit 26a calculates the position of each voxel based on the patient coordinates included in attached information attached to each image, and then calculates a distance between voxels based on the calculated positions.

Figure 3D:
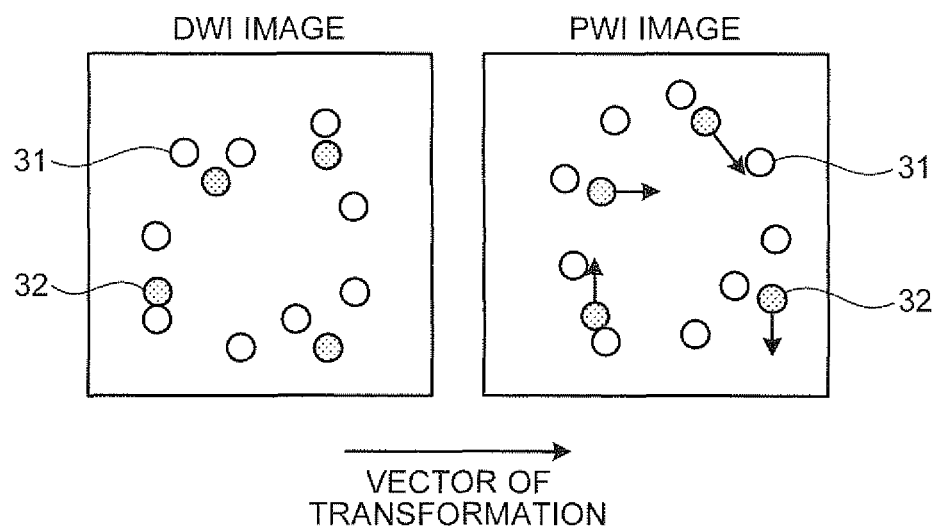

The registration processing unit 26a then registers the position of each voxel by each pair of associated shape voxels. Specifically, as shown in FIG. 3D, the registration processing unit 26a moves the position of each of the shape voxels 32 in the PWI image to match up with the position of a corresponding one of the shape voxels 32 in the DWI image, by each combination of the shape voxels 32, according to the combinations of the shape voxels 32 in which the total of the distances between the voxels is the minimum.

Figure 3E:
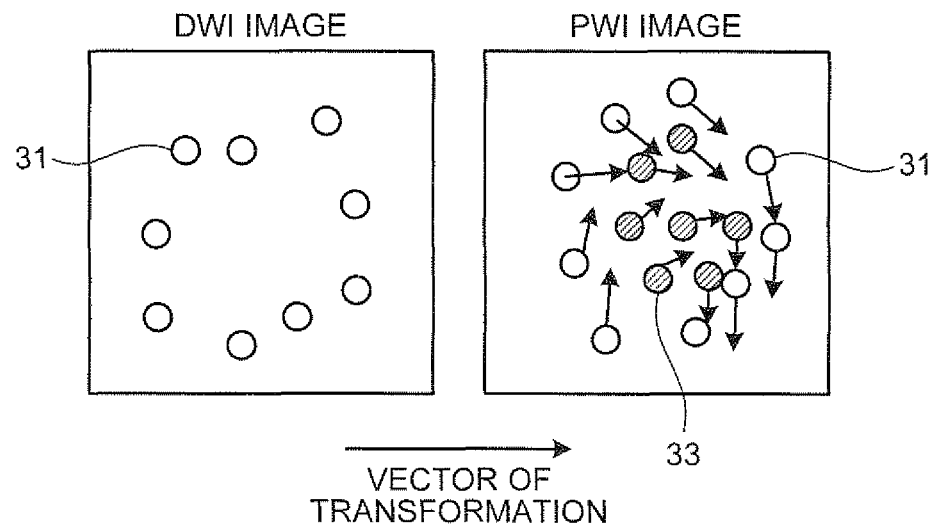

The registration processing unit 26a then registers the position of each voxel included in the region of a portion subjected to registration based on a transformation matrix. Specifically, the registration processing unit 26a calculates the transformation matrix between voxels 33 and the boundary voxels 31 in the region extracted from the PWI image by weighting the transformation of an adjacent shape voxel. The registration processing unit 26a then moves each voxel based on the transformation matrix, as shown in FIG. 3E. Each of the arrows shown in FIGS. 3D and 3E indicates a vector representing the transformation of the transformation matrix.

In this way, the registration processing unit 26a can precisely perform registration of an image that has a distortion, such as a diffusion image and a perfusion image, by changing a style, such as the size and/or the shape, of a portion included in the image subjected to registration.

A method of performing registration of an image is not limited to this. For example, registration of each image can be performed by receiving from an operator an operation of setting an arbitrary number of reference points on each image subjected to registration, and associating the reference points set by the operator. Accordingly, for example, as the operator sets reference points along the contour of the same portion drawn on each image, registration of each image can be performed so as to match up the position of the portion.

Registration of an image is not limited to two-dimensional directions, and can be performed in three-dimensional directions. FIG. 4 is a schematic diagram for explaining of another example of an image registration method performed by the registration processing unit 26a according to the first embodiment. For example, as shown in FIG. 4, it is assumed that six $T_1W$ images $I_{11}$ to $I_{16}$ and five $T_2W$ images $I_{21}$ to $I_{25}$ are taken of the same portion in a slice direction. When each of the images is an axial image, the slice direction is a z-axis direction of the patient coordinate system. When each of the images is a sagittal image, the slice direction is an x-axis direction of the patient coordinate system. When each of the images is a coronal image, the slice direction is a y-axis direction of the patient coordinate system. It is assumed that the $T_1W$ images $I_{11}$ to $I_{16}$ are taken at slice intervals different from those for the $T_2W$ images $I_{21}$ to $I_{25}$. Moreover, it is assumed that the position of the $T_1W$ image $I_1$ matches the position of the $T_2W$ image $I_{21}$, and the position of the $T_1W$ image $I_{16}$ matches the position of the $T_2W$ image $I_{25}$.

In such case, for example, if performing registration between the $T_1W$ image $I_{13}$ and the $T_2W$ image $I_{23}$, the images are different in position in the slice direction. In such case, for example, the registration processing unit 26a creates an interpolation image $I_{33}$ to be in the same position as that of the $T_1W$ image $I_{13}$ in the slice direction by using the $T_2W$ image $I_{22}$ and the $T_2W$ image $I_{24}$ on the opposite sides of the $T_2W$ image $I_{23}$. After that, the registration processing unit 26a performs registration of the interpolation image $I_{33}$ and the $T_1W$ image $I_{13}$ in the direction orthogonal to the slice direction, as required. Any known technology can be used as a method of creating the interpolation image $I_{33}$.

The image-correction processing unit 26b performs a correction of an image registered by the registration processing unit 26a. For example, the image-correction processing unit 26b performs a distortion correction, or a correction for eliminating noise, on an image registered by the registration processing unit 26a. For such correction of an image, any of generally-known various methods of image correction can be used.

The image-correction processing unit 26b can change a display style of each image by performing correction processing. For example, the image-correction processing unit 26b changes the size of each image, or changes the shape of each image.

The ROI setting unit 26c sets an ROI on each image corrected by the image-correction processing unit 26b. For example, to begin with, the ROI setting unit 26c receives an operation of specifying a point of interest on one of a plurality of images displayed on the display unit 25, from the operator via the input unit 24. The ROI setting unit 26c then, sets on the image an ROI of a certain size that has the center at the received point of interest, and applies the same ROI to each of the other images.

Moreover, the ROI setting unit 26c receives an operation of specifying a region (for example, a region of a rectangle or a circle) on one of the images displayed on the display unit 25 via the input unit 24. The ROI setting unit 26c then sets on the image the received region as an ROI, and applies the same ROI to each of the other images.

In this way, when setting an ROI on one of a plurality of images, the ROI setting unit 26c sets similarly the ROI on the other images, thereby omitting procedure of setting point of interest and ROI on each of the images.

The feature-analysis processing unit 26d performs a feature analysis on each image corrected by the image-correction processing unit 26b based on pixel values of pixels included in each ROI set by the ROI setting unit 26c. For example, the feature-analysis processing unit 26d performs a feature analysis by calculating statistics about pixel values, such as an average and a standard deviation of the pixel values.

The display control unit 26e causes the display unit 25 to display each image corrected by the image-correction processing unit 26b in the substantially same position in the display area included in the display unit 25 by switching the images in a certain order as like turning pages, and to display a result of the feature analysis obtained by the feature-analysis processing unit 26d in the same display area.

The display control unit 26e can cause display of a portion of an image on which an ROI is set by the ROI setting unit 26c, for example, in an enlarged manner under a certain magnification. Accordingly, a region subjected to a diagnosis can be more precisely observed.

Figure 6:
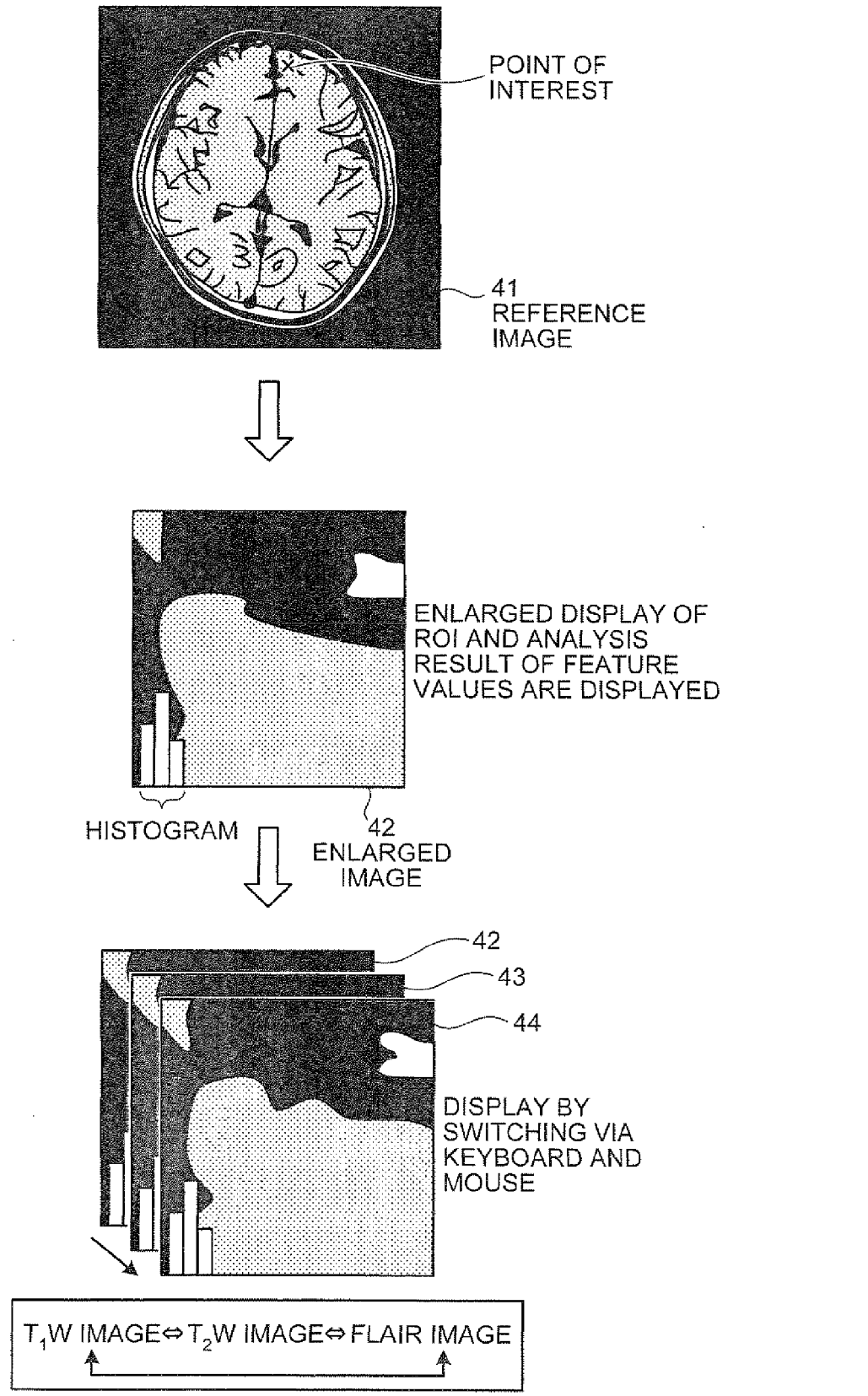
FIG. 6 is a schematic diagram of a flow of image display performed by the control unit according to the first embodiment.

A flow of image display performed by the control unit 26 according to the first embodiment is explained below with reference to FIGS. 5 and 6. FIG. 5 is a flowchart of a process procedure of image display performed by the control unit 26 according to the first embodiment. FIG. 6 is a schematic diagram of a flow of image display performed by the control unit 26 according to the first embodiment. Explained below is an example of processing when displaying a $T_1W$ image, a $T_2W$ image, and a flair image of a brain.

As shown in FIG. 5, according to the control unit 26 of the first embodiment, to begin with, the registration processing unit 26a receives input of a $T_1W$ image, a $T_2W$ image, and a flair image of a brain of the same subject (Step S101), and registers each of the input images (Step S102). The image-correction processing unit 26b then corrects each of the images registered by the registration processing unit 26a (Step S103).

When performing registration, the registration processing unit 26a performs registration of each of the images based on, for example, positional information with respect to a patient coordinate system attached to each image. When performing the registration, the registration processing unit 26a stores the amount of movement of the coordinates generated through the registration into a storage unit, such as an internal memory, with respect to each of the images. If a style of an image, such as the size or the shape, is changed through the correction processing, the image-correction processing unit 26b stores information indicating the size and the shape of the changed image into the storage unit with respect to each of the images.

Subsequently, the display control unit 26e causes the display unit 25 to display one of the images corrected by the image-correction processing unit 26b, for example, the $T_1W$ image, in the display area included in the display unit 25 (Step S104). The image to be displayed at Step S104 is hereinafter referred to as a "reference image". Different images can be set for respective kinds of diseases as a reference image, which can be arbitrarily changed in accordance with an instruction made by the operator.

As shown in FIG. 6, when the operator then specifies a point of interest on a reference image 41 of the displayed $T_1W$ image (Yes at Step S105), the ROI setting unit 26c sets an ROI on each of the images based on the point of interest (Step S106). The example shown in FIG. 6 depicts a case in which an ROI is set on "superior frontal gyrus" in terms of anatomy.

When setting each ROI, the ROI setting unit 26c stores positional information indicating the position of the set ROI into the storage unit with respect to each of the images. Furthermore, the ROI setting unit 26c calculates a magnification when enlarging an image in the set ROI to a certain size for enlarged display, and stores the calculated magnification into the storage unit, with respect to each of the images.

Subsequently, the feature-analysis processing unit 26d creates a histogram of pixel values in the ROI as a feature analysis. For example, the feature-analysis processing unit 26d creates a histogram of statistics, such as an average value and an integrated value of the pixel values (Step S107).

After that, the display control unit 26e creates an enlarged image of the ROI image by image (Step S108), and furthermore, as shown in FIG. 6, causes the display unit 25 to display an enlarged image 42 of the $T_1W$ image on which the histogram created by the feature-analysis processing unit 26d is superimposed, in the display area included, in the display unit 25 (Step S109). For example, the display control unit 26e makes the histogram transparent and superimposes the transparent histogram on the enlarged image 42. The display control unit 26e can make the histogram opaque and superimpose the opaque histogram on the enlarged image 42.

When creating an enlarged image at Step S108, the display control unit 26e specifies the position and the size of the ROI with respect to each of the images based on the amount of movement of the coordinates, information indicating the size and the shape of image changed through correction processing, and positional information about the ROI, which are stored in the storage unit. Moreover, the display control unit 26e creates the enlarged image, image by image, by enlarging an image in the ROI of which the position and the size are specified, based on the magnification stored in the storage unit.

The operator then performs a certain operation of image switching on the displayed enlarged image 42 via the keyboard or the mouse of the input unit 24 (Yes at Step S110), and then the display control unit 26e causes the display unit 25 to display the enlarged image 42 of the $T_1W$ image, an enlarged image 43 of the $T_2W$ image, or an enlarged image 44 of the flair image, on each of which the histogram created by the feature-analysis processing unit 26d is superimposed, by switching the enlarged images, in the substantially same position in the display area included in the display unit 25 (Step S111), as shown in FIG. 6.

FIG. 6 depicts an example when displaying the histogram created from the pixel values of the respective images by arranging it on each of the images. In such case, for example, it can be configured such that the display control unit 26e causes display of a frame of an image and display of a histogram in the same color with respect to each type of image. In such case, for example, the display control unit 26e displays the frame and the histogram of the $T_1W$ image in red, those of the $T_2W$ image in green, and those of the flair image in blue. Accordingly, the operator can easily establish associations between the histograms and the respective images.

As described above, according to the MRI apparatus 100 of the first embodiment, the ROI setting unit 26c included in the control unit 26 sets an ROI on each of a T1W image, a $T_2W$ image, and a flair image of the brain of the subject P. The feature-analysis processing unit 26d creates a histogram of statistics with respect to each of the images based on pixel values of pixels included in the ROIs set by the ROI setting unit 26c. The display control unit 26e then causes the display unit 25 to display one of the images in substantially the same position in the display area included in the display unit 25 by switching the images in a certain order, and to display the histogram created by the feature-analysis processing unit 26d in the same display area. Consequently, according to the first embodiment, change in details due to a difference of the imaging methods can be easily observed without moving the observation point between images. Specifically, by displaying a histogram of statistics together with an image, a diagnosis that is not qualitative but quantitative can be performed.

Figure 7:
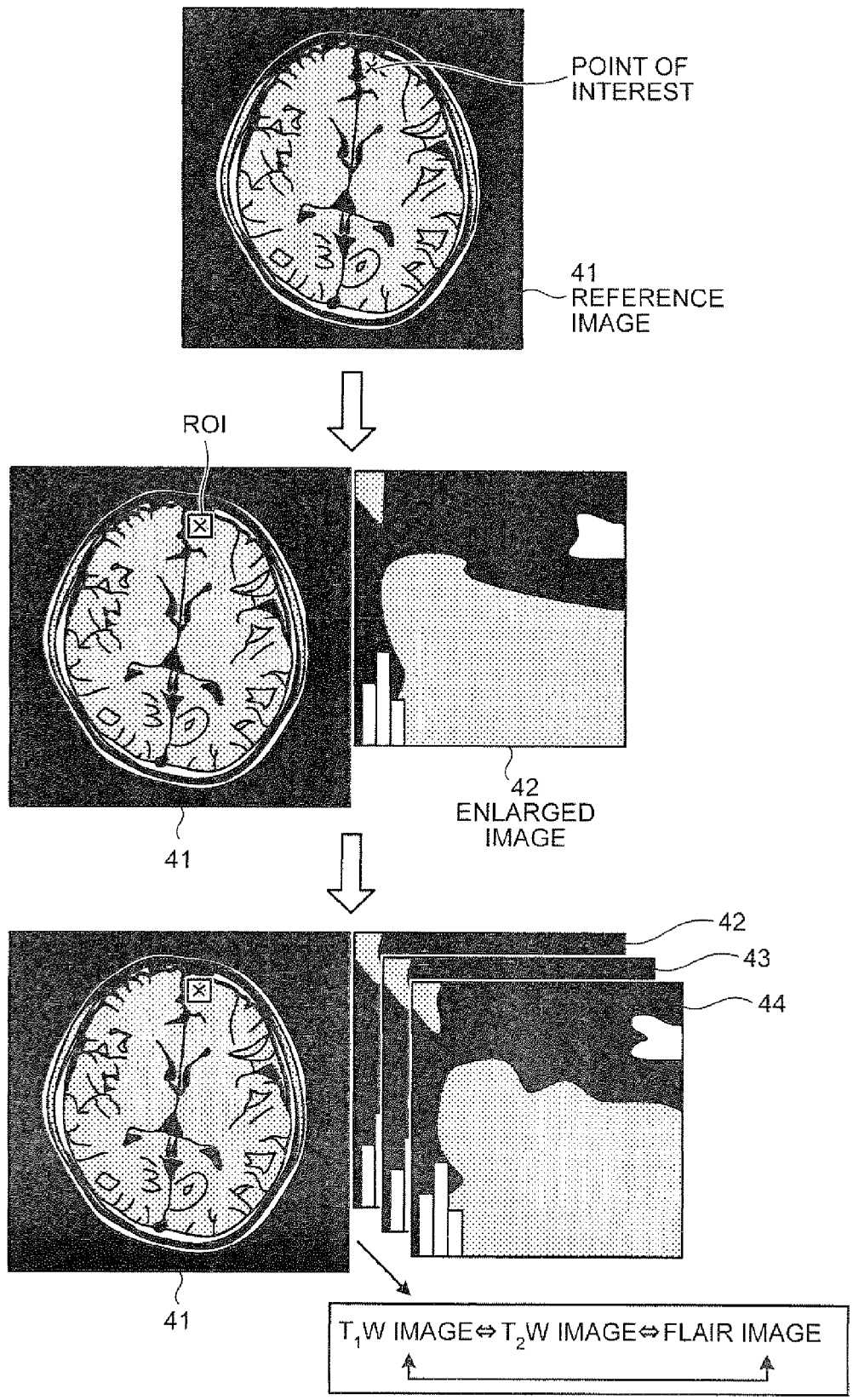
FIG. 7 is a schematic diagram of another flow of image display performed by the control unit according to the first embodiment.

The first embodiment is explained above in a case of displaying only an enlarged image after an ROI is set. However, the present exemplary embodiments are not limited to this, and for example, an embodiment can be configured to display a reference image in parallel with an enlarged image. FIG. 7 is a schematic diagram of another flow of image display performed by the control unit 26 according to the first embodiment.

In this case, for example, as shown in FIG. 7, the display control unit 26e displays the reference image 41 indicating an ROI in parallel with one of the enlarged images 42 to 44. Accordingly, the position of a region displayed in an enlarged manner can be easily grasped in the portion to be examined. For example, a relative position of the ROI in the brain region can be easily grasped.

Moreover, as shown in FIG. 6, the first embodiment is explained above in a case of arranging and displaying a histogram created from pixel values of respective images on each of the images. However, the present exemplary embodiments are not limited to this, and for example, an embodiment can be configured such that the display control unit 26e displays a corresponding result of a feature analysis (a histogram) on each of the images. In such case, the display control unit 26e displays one of results of feature analyses by switching them image by image in accordance with switching of display of the images. Accordingly, the feature values of each of the images can be easily grasped by associating it with the image.

Furthermore, although explained above is a case where the display control unit 26e switches the images in accordance with an operation performed by an operator by using a keyboard and/or a mouse, it can be configured to switch images automatically at certain time intervals. Accordingly, comparative reading of a plurality of images can be performed by switching them even under a situation where the keyboard and the mouse cannot be operated.

Moreover, the display control unit 26e can change the order of switching images in accordance with an instruction from the operator. Accordingly, the operator can change the order of image display so as to perform comparative reading easily in accordance with the type of each image on which the operator performs comparative reading.

The first embodiment is explained above in a case of displaying a $T_1W$ image, a $T_2W$ image, and a flair image of a brain. However, the present exemplary embodiments are not limited to this, and can be similarly applied to a case of displaying other kinds of images.

Conventionally, the usefulness of an evaluation performed in combination on a diffusion image and a perfusion image taken by an MRI apparatus has gained recognition, particularly in examinations of cerebral infarction. Specifically in an examination of cerebral infarction by using a diffusion image and a perfusion image, a segmentation region including a portion in doubt about cerebral infarction is extracted from each of the diffusion image and the perfusion image, and then a region that does not match when superimposing the extracted segmentation regions (hereinafter, "mismatch area") is specified. The specified region is called an "ischemic penumbra area", and considered as a region that can be relieved by an early recovery of blood flow. For this reason, it is meaningful to specify the ischemic penumbra area accurately, for performing a diagnosis and a treatment of cerebral infarction.

A case of displaying a diffusion image and a perfusion image of a brain is explained below as a second embodiment according to the present exemplary embodiments. According to the second embodiment, a diffusion image and a perfusion image are displayed by switching them, while constantly superimposing the boundary of a segmentation region. Accordingly, an ischemic penumbra area can be accurately and easily specified, and a diagnosis and a treatment of cerebral infarction can be promptly performed.

An MRI apparatus according to the second embodiment basically includes a configuration similar to that shown in FIGS. 1 and 2, except that only processing to be performed by the control unit 26 is different; therefore, a flow of image display performed by the control unit 26 is explained below with reference to FIGS. 8 and 9.

Figure 8:
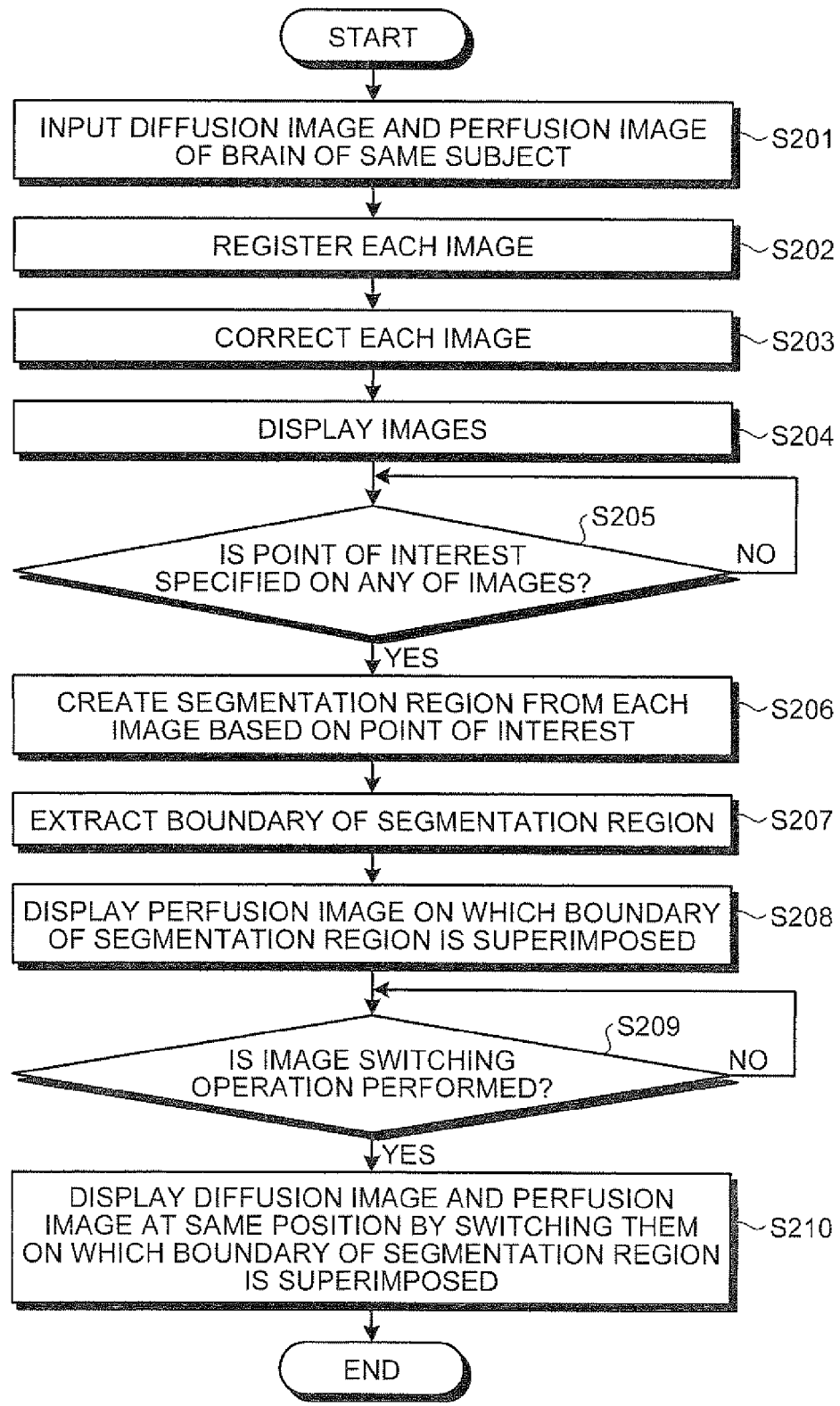
FIG. 8 is a flowchart of a process procedure of image display performed by a control unit according to a second embodiment of the present invention.

FIG. 8 is a flowchart of a process procedure of image display performed by the control unit 26 according to the second embodiment. FIG. 9 is a schematic diagram of a flow of image display performed by the control unit 26 according to the second embodiment. Explained below is an example of processing when displaying separately a diffusion image and a perfusion image of a brain taken at four hours later from an episode of a symptom.

As shown in FIG. 8, according to the control unit 26 of the second embodiment, to begin with, the registration processing unit 26*a* receives input of a diffusion image and a perfusion image of a brain of the same subject taken at four hours later from an episode of a symptom (Step S201), and then registers each of the input images (Step S202). The image-correction processing unit 26*b* then corrects each of the images registered by the registration processing unit 26*a* (Step S203).

When performing registration, the registration processing unit 26*a* performs registration of the images based on, for example, positional information with respect to a patient coordinate system attached to each image. When performing the registration, the registration processing unit 26*a* stores the amount of movement of the coordinates (for example, using a transformation matrix) generated through the registration into a storage unit, such as an internal memory, with respect to each of the images. If a style of an image, such as the size or the shape, is changed through the correction processing, the image-correction processing unit 26*b* stores information that indicates the size and the shape of the changed image into the storage unit with respect to each of the images.

Subsequently, the display control unit 26*e* arranges the images corrected by the image-correction processing unit 26*b*, and then causes the display unit 25 to display the images in the display area included in the display unit 25 (Step S204). As shown in FIG. 9, when the operator specifies a point of interest on one of a diffusion image 51 and a perfusion image 52 both of which are displayed (Yes at Step S205), the ROI setting unit 26*c* sets a point of interest in the same position on the other image on which the operator does not specify point of interest.

Furthermore, the ROT setting unit 26*c* extracts a segmentation region as an ROI from each of the images with reference to a pixel at each point of interest (Step S206). For the extraction of a segmentation region performed at Step S206, one of generally-known various region-extraction methods, for example, a Region Growing method, can be used.

When extracting the segmentation region, the ROI setting unit 26*c* stores positional information indicating the position of the extracted segmentation region into the storage unit with respect to each of the images.

Subsequently, the feature-analysis processing unit 26*d* extracts the boundary of the segmentation region created by the ROI setting unit 26*c* from each of the images as a feature analysis (Step S207).

Figure 9:
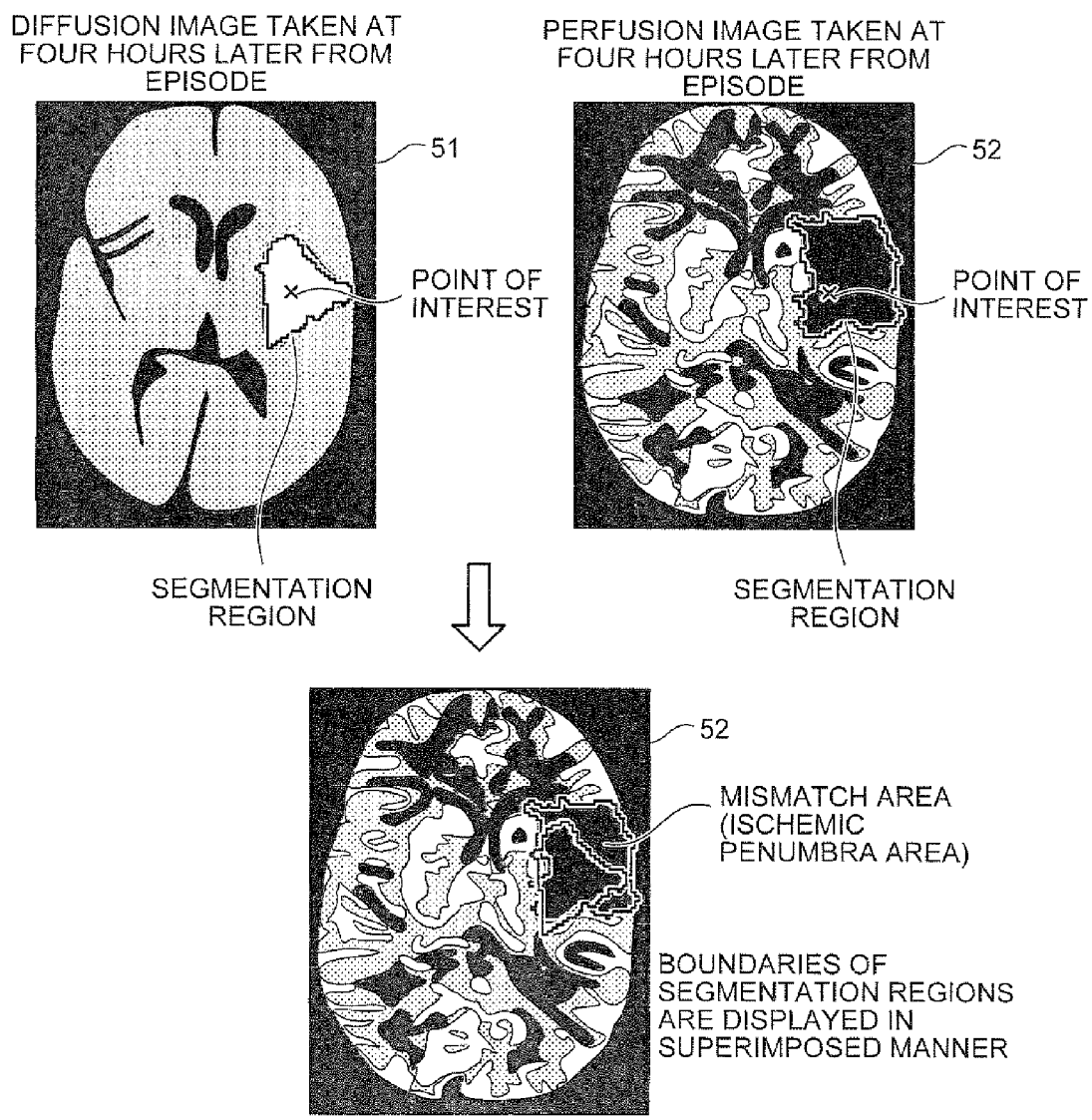
FIG. 9 is a schematic diagram of a flow of image display performed by the control unit according to the second embodiment.

After that, as shown in FIG. 9, the display control unit 26*e* displays the perfusion image 52 on which the segmentation regions extracted from the respective images are superimposed (Step S208). At Step S208, instead of the perfusion image, the display control unit 26*e* can display the diffusion image on which the segmentation regions extracted from the respective images are superimposed.

When superimposing the segmentation regions, the display control unit 26*e* specifies the position of each segmentation region on each image based on the amount of movement of the coordinates, information indicating the size and the shape of image that is changed through correction processing, and positional information about the segmentation region, which are stored in the storage unit; and then superimposes the segmentation regions.

The operator then performs a certain operation of image switching on a displayed image via the keyboard or the mouse of the input unit 24 (Yes at Step S209), and then the display control unit 26*e* causes the display unit 25 to display the diffusion image 51 or the perfusion image 52 on which the segmentation regions extracted from the respective images by the feature-analysis processing unit 26*d* are superimposed, by switching the images, in the substantially same position in the display area included in the display unit 25 (Step S210). FIG. 9 depicts an example of the perfusion image 52 on which the segmentation regions are superimposed.

As described above, according to the second embodiment, in the MRI apparatus 100, the ROI setting unit 26*c* included in the control unit 26 creates segmentation regions from a diffusion image and a perfusion image of a brain as an ROI by performing certain region-extracting processing; and the feature-analysis processing unit 26*d* extracts a boundary of each segmentation created by the ROI setting unit 26*c* with respect to each of the images, as a feature analysis. The display control unit 26*e* then superimposes one on another of respective boundaries of the segmentation regions in the respective images extracted by the feature-analysis processing unit 26*d*, and causes display of the superimposed boundaries on an image in a superimposed manner. In consequence, according to the second embodiment, because a region indicated by using segmentation regions in a plurality of images, for example, an ischemic penumbra area in a brain, can be accurately and easily specified, a diagnosis and a treatment can be promptly and effectively performed.

Figure 10:
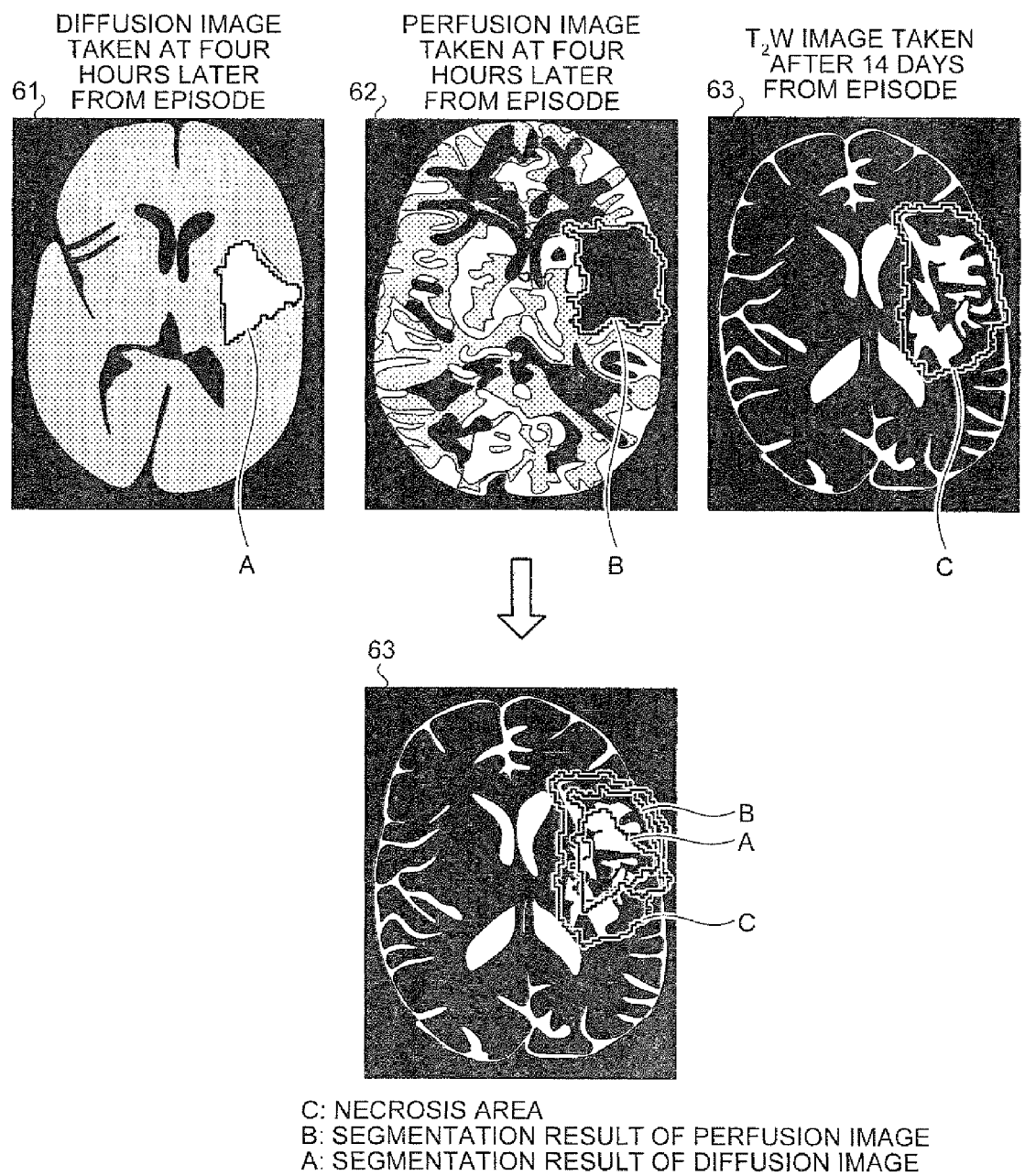
FIG. 10 is a schematic diagram of another flow of image display performed by the control unit according to the second embodiment.

The second embodiment is explained above in a case of displaying a diffusion image and a perfusion image taken at the same timing (four hours later from an episode of a symptom). However, the present invention is not limited to this, and, for example, can be similarly applied to a case of displaying a plurality of images taken at different timings. FIG. 10 is a schematic diagram of another flow of image display performed by the control unit 26 according to the second embodiment.

For example, as shown in FIG. 10, when displaying a diffusion image 61 taken at four hours later from an episode of a symptom, a perfusion image 62 taken at four hours later from the episode, and a T$_2$W image 63 taken after 14 days from the episode, the display control unit 26*e* superimposes a boundary A of a segmentation region extracted from the diffusion image 61, a boundary B of a segmentation region extracted from the perfusion image 62, and a boundary C of a segmentation region extracted from the T$_2$W image 63, on the respective images, and then displays each of the images by switching them. The boundary C indicates a region in which tissue is necrosis. FIG. 10 depicts an example of the T$_2$W image 63 taken after 14 days from the episode on which the boundaries A to C are superimposed.

In this way, by constantly displaying the boundary of a segmentation region in a tissue image (for example, a T$_2$W image) taken after the elapse of a certain time from an episode of a symptom, and further displaying the boundary of a segmentation in a functional image (for example, a diffusion image and/or a perfusion image) taken immediately after the episode in a superimposed manner, a progress of the symptom about a lesion portion from immediately after the episode can be efficiently observed.

Furthermore, the display control unit 26e can vary the colors of the boundaries when displaying the boundaries in a superimposed manner. Accordingly, each of the boundaries can be easily identified.

Although the first embodiment and the second embodiment are explained above in cases where the present invention is applied to an MRI apparatus, the present invention is not limited to this, and can be similarly applied to other diagnostic imaging apparatuses. The present invention can be similarly applied to, for example, an X-ray diagnosis apparatus, an X-ray Computed Tomography (CT) apparatus, an ultrasound diagnosis apparatus, a Single Photon Emission Computed Tomography (SPECT) apparatus, and a Positron Emission Tomography (PET) apparatus.

Moreover, the first embodiment and the second embodiment are explained above in cases where after performing registration of a plurality of images, a segmentation region is extracted from each of the images, and then the extracted segmentation regions are displayed on each of the images in a superimposed manner. In contrast, for example, before registration of the images, a segmentation region is extracted from each of the images, and then registration can be performed only between the extracted segmentation regions.

In such case, for example, at first, the display control unit 26e registers one with another of segmentation regions extracted from respective images by the feature-analysis processing unit 26d, and then superimposes them one on another. The display control unit 26e then performs registration of the superimposed segmentation regions with an image to be displayed, and then superimposes them one on another and displays them. Accordingly, registration of the whole image does not need to be performed with respect to each of the images, so that the load of processing related to the registration can be reduced.

Furthermore, the first embodiment and the second embodiment are explained above in cases where the present invention is applied to an MRI apparatus; however, the present invention is not limited to this, and can be similarly applied to an image display apparatus (also called a viewer) that displays images taken by various diagnostic imaging apparatuses, such as an MRI apparatus, an X-ray diagnosis apparatus, an X-ray CT apparatus, an ultrasound diagnosis apparatus, a SPECT apparatus, a PET apparatus, and an endoscope.

Figure 11:
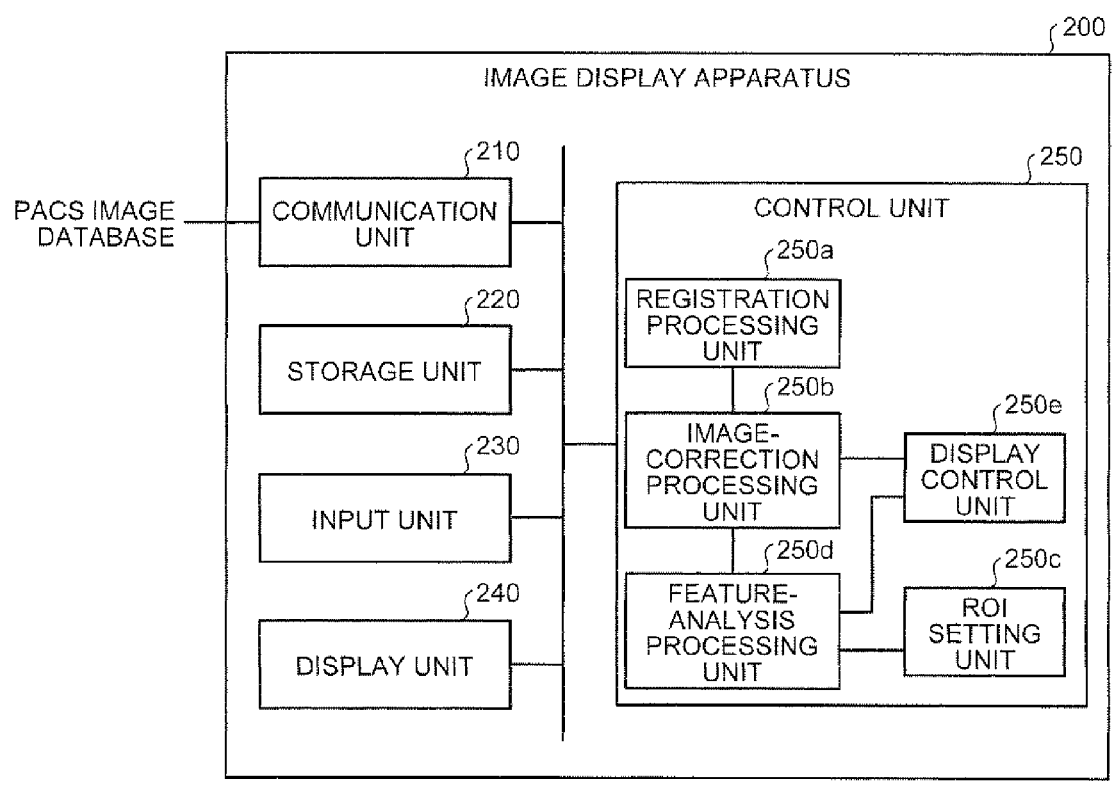
FIG. 11 is a functional block diagram of a configuration of an image display apparatus according to a third embodiment of the present invention.

A case of applying the present invention to an image display apparatus is explained below as a third embodiment according to the present exemplary embodiments. At first, a configuration of the image display apparatus according to the third embodiment is explained below with reference to FIG. 11. FIG. 11 is a functional block diagram of a configuration of an image display apparatus 200 according to the third embodiment. As shown in FIG. 11, the image display apparatus 200 according to the third embodiment includes a communication unit 210, a storage unit 220, an input unit 230, a display unit 240, and a control unit 250.

The communication unit 210 controls transmission and reception of information that is exchanged between the image display apparatus 200 and a Picture Archiving and Communication System (PACS), an image database, or the like, via a network. The PACS is an image administration system included in various diagnostic imaging apparatuses and image storage devices connected via a network. The image database is a database that stores various images taken by various diagnostic imaging apparatuses.

Such image data transmitted from the PACS or the image database are typically tomographic images or projection images, and further includes tomographic images of multiple cross sections, and volume data expressed with voxels. Moreover, the transmitted image data can be data of before image creation. For example, an MRI apparatus sometimes performs registration in some cases by calculating the amount of movement by measuring correlation between data in frequency space. Furthermore, such image data can be attached with information, such as imaging parameters, slice (scanning) position, imaging time, and imaging conditions.

The storage unit 220 stores various information, for example, an image received from the PACS or an image database via the communication unit 210, and various programs to be executed by the control unit 250.

The input unit 230 receives various instructions and information input from an operator. A pointing device, such as a mouse or a trackball, and an input device, such as a keyboard, can be used as the input unit 230, as required.

The display unit 240 displays various information, such as an image taken by a diagnostic imaging apparatus. A display device, such as a liquid crystal display, can be used as the display unit 240, as required.

The control unit 250 includes a CPU and a memory, both of which are not shown, and carries out total control of the image display apparatus 200. According to the third embodiment, control unit 250 sets an ROI on each of a plurality of images that includes the same portion of a subject, and performs a feature analysis on each of the images based on pixel values of pixels included in the set ROI. The control unit 250 then causes display unit 240 to display each of the images in substantially the same position in a display area included in display unit 240 by switching the images in a certain order, and to display a result of the feature analysis in the same display area. Consequently, according to the third embodiment, change in details due to a difference of the imaging methods can be easily observed without moving the observation point between images.

Specifically, the control unit 250 particularly includes a registration processing unit 250a, an image-correction processing unit 250b, an ROI setting unit 250c, a feature-analysis processing unit 250d, and a display control unit 250e. Respective functions of the units are basically similar to those of the registration processing unit 26a, the image-correction processing unit 26b, the ROI setting unit 26c, the feature-analysis processing unit 26d, and the display control unit 26e shown in FIG. 2, therefore, detailed explanations are omitted below.

Figure 12:
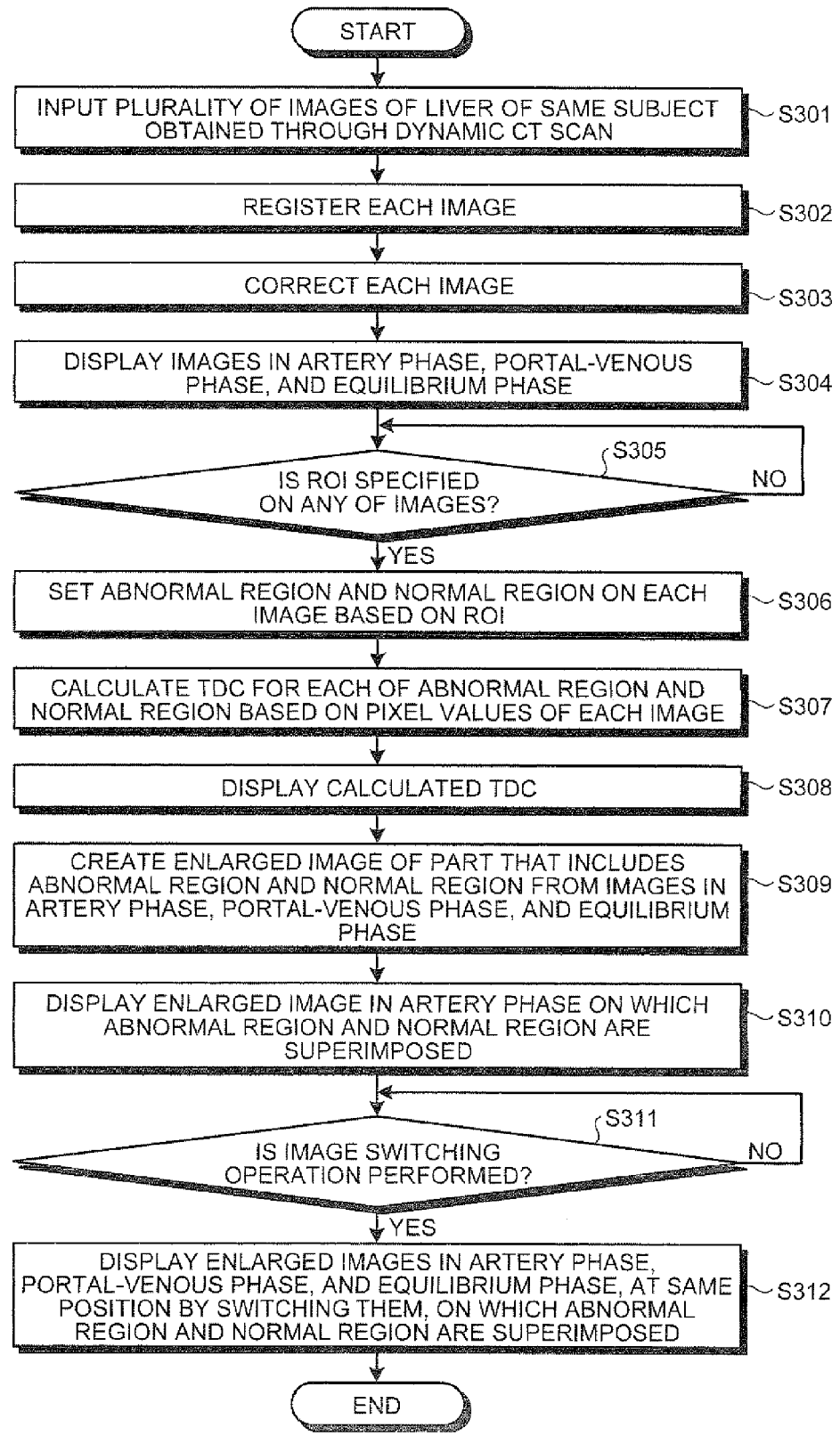
FIG. 12 is a flowchart of a process procedure of image display performed by a control unit according to the third embodiment.
Figure 13:
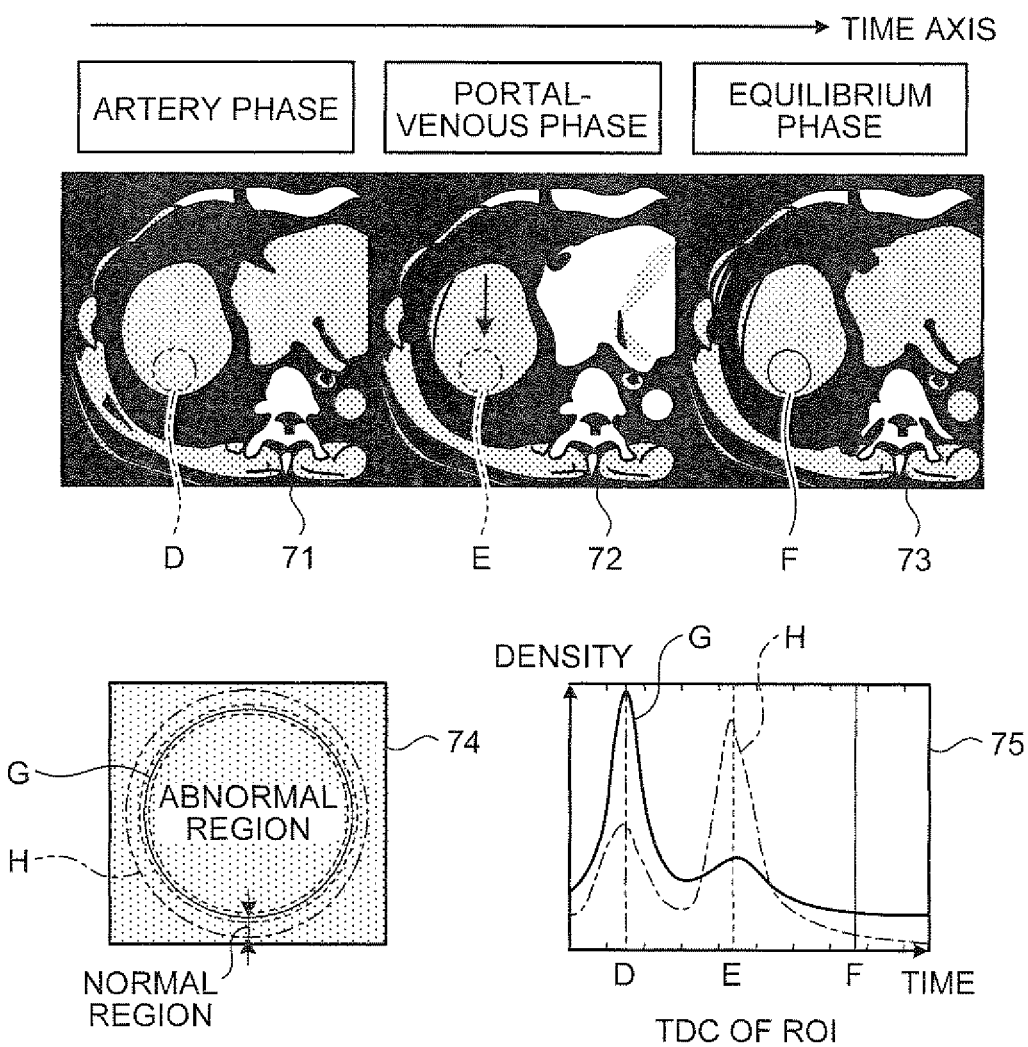
FIG. 13 is a schematic diagram of a flow of image display performed by the control unit according to the third embodiment.

A flow of image display performed by the control unit 250 according to the third embodiment is explained below with reference to FIGS. 12 and 13. FIG. 12 is a flowchart of a process procedure of image display performed by the control unit 250 according to the third embodiment. FIG. 13 is a schematic diagram of a flow of image display performed by the control unit 250 according to the third embodiment. Explained below is an example of processing when displaying images of a liver taken along a time sequence by dynamic imaging with the use of an X-ray CT apparatus (hereinafter, "dynamic CT scan").

According to dynamic imaging of a liver, imaging is carried out at a plurality of different timings after a contrast agent is injected into a subject. The timings include an artery phase, a portal-venous phase, and an equilibrium phase. The equilibrium phase is the late phase of enhancement after several minutes. The concentration of residual contrast agent in each of the phases is meaningful information. The third embodiment is explained below in a case of displaying respective images of the liver in the artery phase, the portal-venous phase, and the equilibrium phase, obtained through a dynamic CT scan.

As shown in FIG. 12, according to the control unit 250 of the third embodiment, to begin with, the registration processing unit 250a receives input of respective images of a liver of the same subject in an artery phase, a portal-venous phase, and an equilibrium phase, obtained through a dynamic CT scan (Step S301), and registers each of the input images (Step S302). The registration processing of images performed at Step S302 can be omitted. Accordingly, a processing time for calculation can be reduced.

The image-correction processing unit 250b then corrects each of the images registered by the registration processing unit 250a (Step S303).

Subsequently, as shown in FIG. 13, the display control unit 250e causes the display unit 240 to display an image 71 in the artery phase of the liver, an image 72 in the portal-venous phase, and an image 73 in the equilibrium phase, each of which is corrected by the image-correction processing unit 250b, in an arranged manner in the display area included in the display unit 240 (Step S304).

As shown in FIG. 13, when the operator then specifies an ROI on one of the image 71 in the artery phase, the image 72 in the portal-venous phase, and the image 73 in the equilibrium phase (D on the image 71, E on the image 72, or F on the image 73) (Yes at Step S305), the ROI setting unit 250c similarly sets the ROI in the same position on each of the images in the other phases on which the operator does not specify ROI.

Subsequently, the feature-analysis processing unit 250d sets an abnormal area and a normal area on each of the images based on the ROI set by the ROI setting unit 250c (Step S306). Specifically, as shown in FIG. 13, the feature-analysis processing unit 250d sets the ROI set by the ROI setting unit 250c to an abnormal area, and sets an extended area extended from the abnormal area by a certain distance to a normal area.

The feature-analysis processing unit 250d then calculates a Time Density Curve (TDC) of each of the abnormal area and the normal area based on pixel values of each of the images, as a feature analysis (Step S307). At Step S307, the feature-analysis processing unit 250d can calculate a TDC that indicates pixel values, otherwise can calculate a TDC that indicates differences from reference values that are pixel values of an image taken before a contrast agent is injected.

After that, as shown in FIG. 13, the display control unit 250e causes the display unit 240 to display a graph 75 of the TDCs created by the feature-analysis processing unit 250d in the display area included in the display unit 240 (Step S308). According to the graph 75, a curve H denotes the TDC of the normal area, and a curve G denotes the TDC of the abnormal area.

As shown in FIG. 13, the display control unit 250e can display the respective ROIs set on the image 71 in the artery phase, the image 72 in the portal-venous phase, and the image 73 in the equilibrium phase (regions D, E, F, on the images 71 to 73) and respective lines indicating the artery phase, the portal-venous phase, and the equilibrium phase in the graph 75 of the TDCs (lines D, F, and F) in the same colors phase by phase. Accordingly, the image in each phase and the concentration in each phase (corresponding to the level of a pixel value) can be easily observed in an associated manner.

Subsequently, the display control unit 250e creates enlarged images including the abnormal area and the normal area respectively from the image 71 in the artery phase, the image 72 in the portal-venous phase, and the image 73 in the equilibrium phase (Step S309); and then causes the display unit 240 to display an enlarged image 74 in the artery phase on which the abnormal area and the normal area set by the ROI setting unit 250c are superimposed in the display area included in the display unit 240 (Step S310). Otherwise the display control unit 250e can cause display of an enlarged image in the portal-venous phase or in the equilibrium phase, instead of the enlarged image 74 in the artery phase.

When the operator performs a certain operation of image switching on a displayed image via the keyboard or the mouse of the input unit 230 (Yes at Step S311), the display control unit 250e causes the display unit 240 to display one of the respective enlarged images in the artery phase, the portal-venous phase, and the equilibrium phase, on each of which the abnormal area and the normal area set by the ROT setting unit 250c are superimposed, by switching the enlarged images, in the substantially same position in the display area included in the display unit 240 (Step S312).

As shown in FIG. 13, the display control unit 250e can display a line indicating the abnormal area on the enlarged image (line G on the enlarged image 74) and a curve indicating the TDC of the abnormal area in the graph 75 of the TDCs (curve G in the graph 75) in the same color, and a line indicating the normal area on the enlarged image (line H on the enlarged image 74) and a curve indicating the TDC of the normal area in the graph 75 of the TDCs (curve H in the graph 75) in the same color. Accordingly, the curves in the graph 75 of the TDCs and the abnormal area and the normal area superimposed on the image 71 in the artery phase, the image 72 in the portal-venous phase, and the image 73 in the equilibrium phase can be easily observed in an associated manner.

Alternatively, one of the regions D, E, and F in FIG. 13 corresponding to a switched and displayed image can be displayed in a highlighted manner.

As described above, according to the third embodiment, in the image display apparatus 200, the ROI setting unit 250c of the control unit 250 sets an ROI on each of a plurality of images of a liver obtained through a dynamic CT scan; and the feature-analysis processing unit 250d sets an abnormal area and a normal area on each of the images based on pixel values of pixels included in the ROI set by the ROI setting unit 250c, and calculates TDCs of the set abnormal area and the set normal area. The display control unit 250e then causes the display unit 240 to display the images in substantially the same position in the display area included in the display unit 240 by switching the images in a certain order, and to display the abnormal area and the normal area, and the TDCs of the respective areas, in the same display area. Consequently, according to the third embodiment, change in details due to a difference of the imaging methods can be easily observed without moving the observation point between images. Specifically, the degree of remaining contrast agent in a liver can be visually confirmed.

In addition to the image used in the above embodiments, the image switching display and the display of feature values of ROI described in the above embodiments can be similarly applied to, for example, a plurality of CT images, MR images, ultrasound images, SPECT images, PET images, and endoscope images, taken under different imaging conditions (including imaging time). Moreover, the above display can be similarly applied to display of a combined image of some of those images. Examples of such combination include CT and MR, CT and PET, CT and SPECT, Digital Subtraction Angiographies (DSA) and MR, PET and MR, PET and an ultrasound diagnosis apparatus (US), SPECT and MR, SPECT and US, US and CT, US and MR, an X-ray diagnosis apparatus (X-ray) and CT, X-ray and MR, and X-ray and US.

As described above, according to the first, the second, or the third embodiment, a plurality of kinds of images taken of the same portion through various methods is displayed in substantially the same position on a screen by being switched, and feature values are additionally displayed; so that change in details due to a difference of imaging methods can be easily observed while fixing an observation point at a screen position of a portion of interest. Accordingly, an image reader can improve the efficiency of image reading, and can perform a diagnosis and a treatment promptly. Moreover, because a statistical result is also displayed, a diagnosis that is not qualitative but quantitative can be performed.

In other words, according to the first, the second, or third embodiment, by displaying an image effective for an image diagnosis and its feature values, with the use of a plurality of medical images, anatomical details (ROI) on each image can be comparatively read without moving the observation point, and determination of presence or absence of a disease, screening between benign and malign characteristics, and a decision about a treatment flow, can be performed.

As described above, the image display apparatus, the image display method, and the magnetic resonance imaging apparatus according to the embodiments of the present invention are useful when performing comparative reading of various images, and particularly suitable when one needs to perform a quantitative diagnosis based on a grasp of features of various images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising: a computer system including at least one central processing unit (CPU) and associated memory, an image data input port and a visual display, said memory containing executable program instructions which, when executed by said CPU, effect:
    creation of a plurality of segmentation regions, based on analysis of pixel values in the images, by applying a prescribed region extraction processing to each of a plurality of different kinds of images including a same portion of a subject imaged by a diagnostic imaging apparatus;
    extraction of a plurality of boundaries of the segmentation regions from at least two of the images as displayable visually discernable edges of the segmentation regions;
    superposition of the extracted plurality of the visually discernable edges of the segmentation regions on respective ones of the images;
    concurrently displaying the extracted plurality of visually discernable edge boundaries of the segmentation regions in fixed overlapping superimposed respective positions on the visual display; and
    switching the images in a prescribed order on the visual display causing each image to be displayed in sequence with its segmentation region positioned within a respectively associated one of the concurrently displayed superimposed extracted plurality of visually discernable edge boundaries.

2. The image display apparatus according to claim 1, wherein said program instructions are further configured, when executed by said CPU, to perform registration between the images, wherein the extracted plurality of boundaries of the segmentation regions are superimposed by specifying a position of each of the segmentation regions on each of the images based on (a) an amount of movement of coordinates generated through the registration and (b) positional information about each of the segmentation regions.

3. The image display apparatus according to claim 1, wherein the images include images taken by different imaging methods.

4. The image display apparatus according to claim 1, wherein the images include images taken along a time sequence.

5. The image display apparatus according to claim 1, wherein the images include images taken by one diagnostic imaging apparatus or by different diagnostic imaging apparatuses.

6. The image display apparatus according to claim 1, wherein the images include images taken by a magnetic resonance imaging apparatus under imaging conditions that include respectively different imaging parameter values.

7. The image display apparatus according to claim 6, wherein the imaging conditions include respectively different echo times.

8. The image display apparatus according to claim 6, wherein the imaging conditions include respectively different repetition times.

9. The image display apparatus according to claim 6, wherein the imaging conditions include respectively different b factor values that indicate strength of a Motion Probing Gradient (MPG) pulse.

10. An image display method comprising:
    using at least one computer processor including input and output ports, at least one data store and an associated display to:
    create a plurality of segmentation regions, based on analysis of pixel values in the images, by applying region extraction processing to each of a plurality of different kinds of images including a same portion of a subject imaged by a diagnostic imaging apparatus;
    extract a plurality of boundaries of the segmentation regions from at least two of the images as displayable visually discernable edges of the segmentation regions;
    superimpose the extracted plurality of visually discernable edge boundaries of the segmentation regions;
    concurrently display the extracted plurality of visually discernable edge boundaries of the segmentation regions in fixed overlapping superimposed respective positions on the display; and
    switch the images in a prescribed order on the display causing each image to be displayed in sequence with its segmentation region positioned within a respective associated one of the concurrently displayed superimposed extracted plurality of visually discernable edge boundaries.

11. A magnetic resonance imaging (MRI) apparatus comprising:
    an MRI gantry having static and gradient magnets, at least one radio-frequency (RF) coil and an interconnected computer control system configured to acquire a plurality of different kinds of images including a same portion of a subject;

at least one central processing unit (CPU) and associated memory having program instructions which, when executed by said CPU, creates a plurality of segmentation regions, based on pixel values of pixels in said images, by applying region extraction processing to each of the images;

said at least one CPU also being controlled by said program instructions to extract a plurality of boundaries of the segmentation regions from at least two of the images as displayable visually discernable edges of the segmentation regions;

said at least one CPU also being controlled by said program instructions to (a) superimpose the extracted plurality of visually discernable edge boundaries of the segmentation regions on a display in fixed overlapping respective positions and (b) display the images one at a time with the image segmentation region positioned within a respectively associated one of the concurrently displayed superimposed extracted plurality of visually discernable edge boundaries.

* * * * *